(12) United States Patent
Guo et al.

(10) Patent No.: US 12,138,450 B2
(45) Date of Patent: *Nov. 12, 2024

(54) DELIVERY DEVICE HAVING A DEFLECTABLE AND PEELABLE MAPPING GUIDE SHEATH FOR HIS BUNDLE PACING

(71) Applicant: St. Jude Medical, Cardiology Division, Inc., St. Paul, MN (US)

(72) Inventors: Xiaoping Guo, Eden Prairie, MN (US); Erich W. Stoermer, Plymouth, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 254 days.

This patent is subject to a terminal disclaimer.

(21) Appl. No.: 17/857,229

(22) Filed: Jul. 5, 2022

(65) Prior Publication Data

US 2022/0347463 A1   Nov. 3, 2022

Related U.S. Application Data

(63) Continuation of application No. 16/452,223, filed on Jun. 25, 2019, now Pat. No. 11,413,454.

(51) Int. Cl.
*A61N 1/00* (2006.01)
*A61M 25/06* (2006.01)
*A61N 1/05* (2006.01)
*A61M 25/01* (2006.01)

(52) U.S. Cl.
CPC ......... *A61N 1/059* (2013.01); *A61M 25/0668* (2013.01); *A61N 1/056* (2013.01); *A61M 25/0108* (2013.01); *A61M 2025/0681* (2013.01)

(58) Field of Classification Search
None
See application file for complete search history.

(56) References Cited

U.S. PATENT DOCUMENTS

| 4,883,468 A | 11/1989 | Kousai et al. |
| 5,030,204 A | 7/1991 | Badger et al. |
| 5,320,602 A | 6/1994 | Karpiel |

(Continued)

FOREIGN PATENT DOCUMENTS

WO     0172368 A2    10/2001

*Primary Examiner* — John R Downey
*Assistant Examiner* — Anant A Gupta
(74) *Attorney, Agent, or Firm* — Dean D. Small; The Small Patent Law Group, LLC

(57) ABSTRACT

A delivery device for delivering a pacing lead to the His bundle of a patient's heart includes an elongated sheath having a distal end, and a plurality of mapping electrodes positioned at the distal end. The distal end of the sheath may have a distal end face, and the mapping electrodes may include two electrodes that diametrically oppose one another at a position exposed on or spaced from the distal end face. The sheath includes a plurality of flexible sections spaced apart from one another, and a pull wire that causes the sheath to deflect from a substantially straight configuration to a dual hinged curved configuration that maneuvers and positions the electrodes in the vicinity of the bundle of His. The sheath may include a PTFE liner having axially oriented, platelet-like fibril features that enable the sheath to be split along its length from a proximal end to the distal end.

20 Claims, 20 Drawing Sheets

(56) References Cited

U.S. PATENT DOCUMENTS

| | | | |
|---|---|---|---|
| 5,752,937 A * | 5/1998 | Otten | A61M 25/0668 |
| | | | 604/161 |
| 7,369,901 B1 | 5/2008 | Morgan et al. | |
| 7,377,909 B2 | 5/2008 | Rickerd | |
| 8,449,527 B2 | 5/2013 | Thorstenson et al. | |
| 9,937,319 B1 * | 4/2018 | Leeflang | A61M 25/0668 |
| 2004/0215139 A1 * | 10/2004 | Cohen | A61N 1/056 |
| | | | 604/95.04 |
| 2008/0008688 A1 | 1/2008 | Stokes et al. | |
| 2013/0018309 A1 | 1/2013 | Ewing et al. | |
| 2016/0317220 A1 | 11/2016 | Guo | |

* cited by examiner

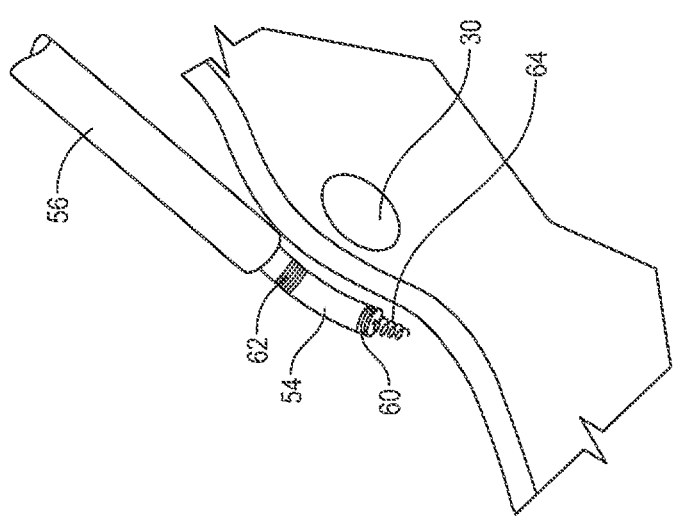
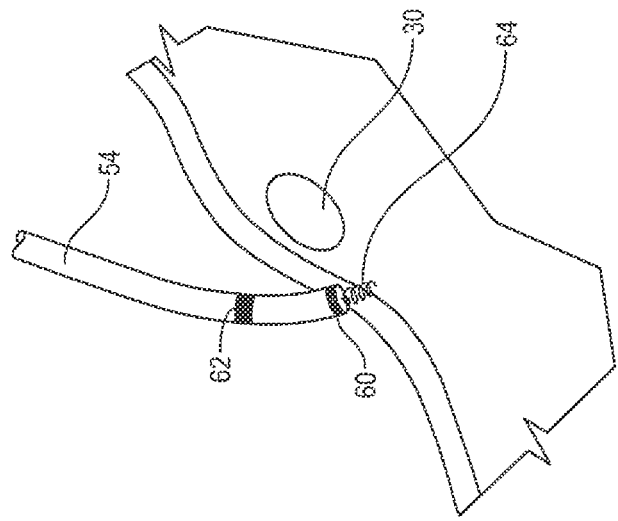
FIG. 3
(PRIOR ART)

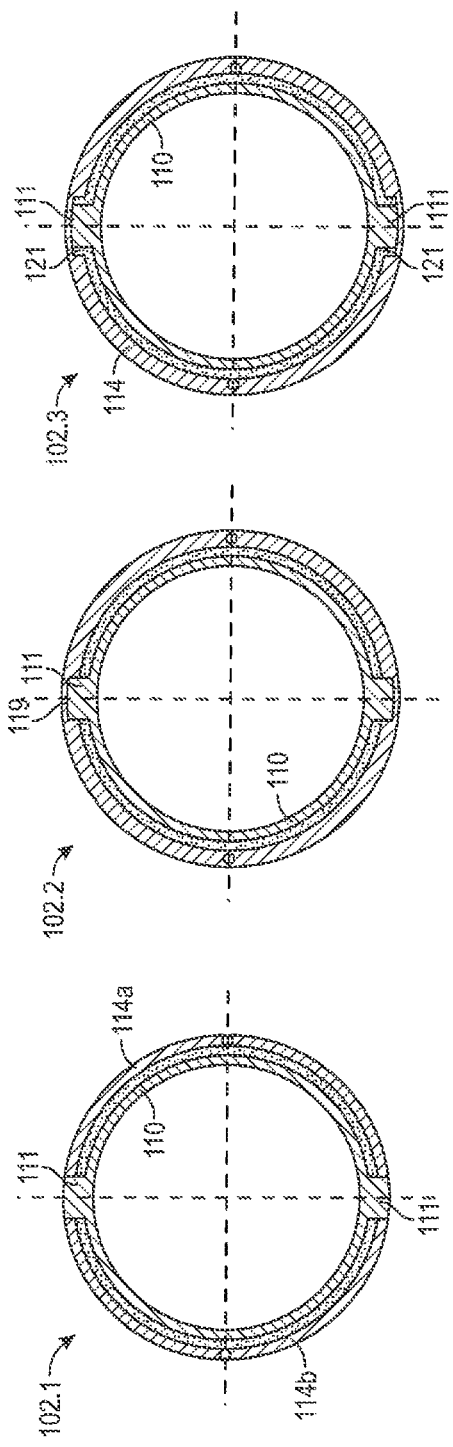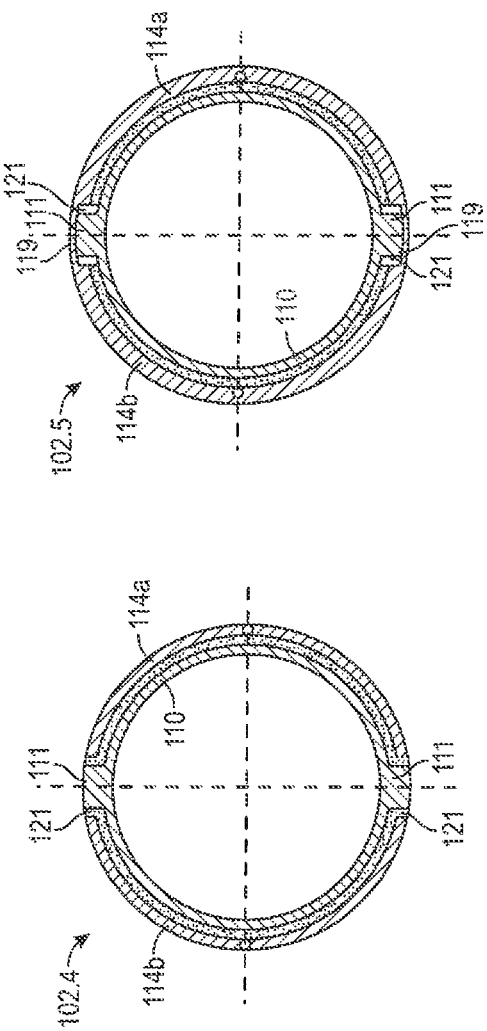

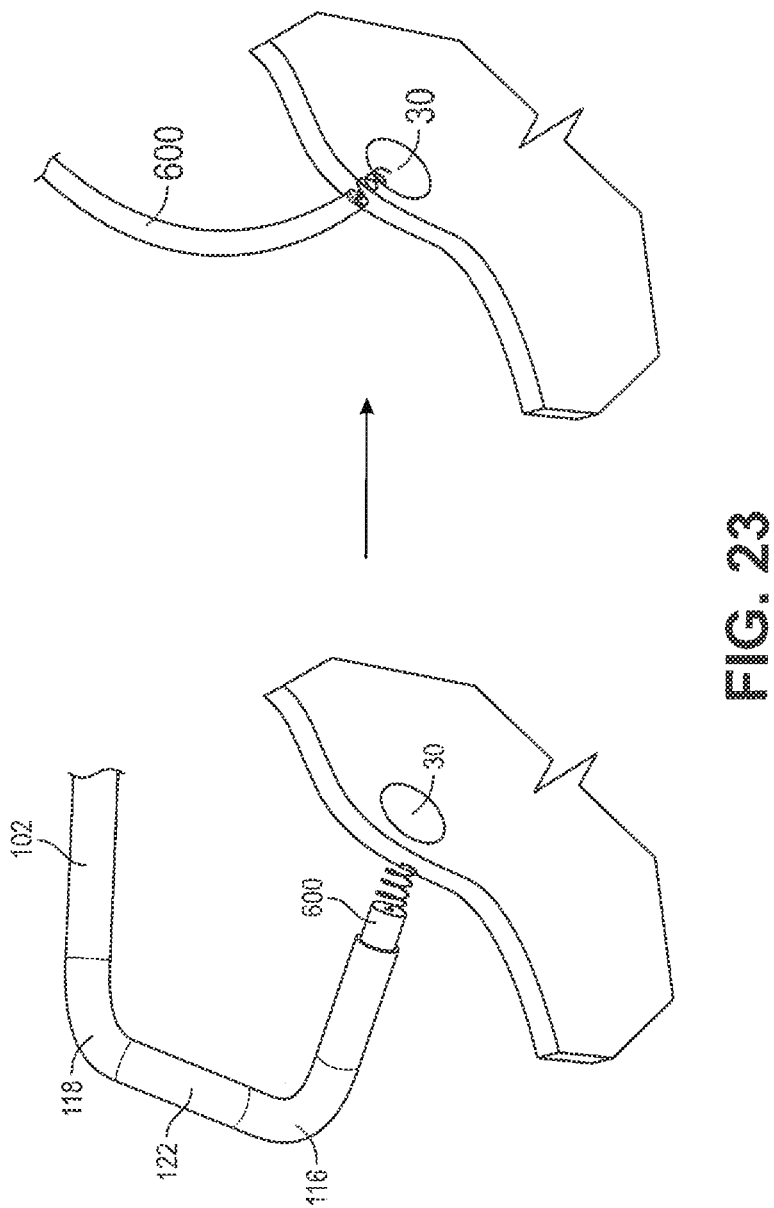

DELIVERY DEVICE HAVING A DEFLECTABLE AND PEELABLE MAPPING GUIDE SHEATH FOR HIS BUNDLE PACING

REFERENCE TO RELATED APPLICATIONS

The present application is a continuation application of, and claims priority to, U.S. application Ser. No. 16/452,223, Titled "DELIVERY DEVICE HAVING A DEFLECTABLE AND PEELABLE MAPPING GUIDE SHEATH FOR HIS BUNDLE PACING" which was filed on 25 Jun. 2019, the complete subject matter of which is expressly incorporated herein by reference in its entirety.

The present disclosure relates to cardiac resynchronization therapy (CRT), and more particularly to a delivery device comprising a deflectable and peelable mapping guide sheath for locating the bundle of His and guiding an electrode lead thereto. Still more particularly, the present invention relates to a deflectable and peelable mapping guide sheath that is readily removable from the patient.

BACKGROUND OF THE INVENTION

Cardiac rhythm management systems are useful for electrically stimulating a patient's heart to treat various cardiac arrhythmias. The current standard of care is to pace the right ventricle by myocardial stimulation. In this technique, pacemaker leads are placed at the apex of the right ventricle and at the AV node, the coronary sinus or the left ventricle, and a pacemaker sends electrical pulses to these areas of the heart. While effective, this technique can cause abnormal electrical activation sequences resulting in mechanical ventricular dyssynchrony and an increased risk of heart failure, atrial fibrillation and overall mortality.

An alternative approach has been proposed in which an electrode lead is placed into the bundle of His located either in the septal wall of the right atrium or subvalvular from the right ventricle also in the atrial septum. As part of the electrical conduction system of the heart, the bundle of His transmits electrical impulses from the atrioventricular (AV) node to the ventricles of the heart. As the electrical impulses that regulate the heartbeat are conducted through the bundle of His from the right atrium to the left and right ventricles, a lead placed in or in close proximity to the bundle of His would enable the entire electrical conduction system to be paced in a physiologically natural way. Pacing the ventricles in this manner, which closely mimics normal AV conduction, can greatly reduce or eliminate the risks associated with traditional CRT pacing.

While the improved results obtainable with His pacing have been recognized, in practice His pacing is difficult to achieve because the bundle of His is very small and difficult to locate and access with the use of available or conventional lead delivery devices. The bundle of His has a nominal length of about 5 mm and a nominal width of about 2 mm. As compared to the ventricles, it generates a relatively faint electrical signal. As a result of its small size and weak electrical signal, the bundle of His is extremely difficult to locate by a conventional lead delivery method. Moreover, once the bundle of His has been located, it is difficult using a conventional lead delivery device to maintain the position of the lead while it is being affixed to the cardiac tissue. The difficulties involved in locating the bundle of His and affixing a pacing lead thereto are reflected in the time it takes to implant the leads of an electrical stimulation device, such as a pacemaker. In a typical case, implanting biventricular leads can be completed in as little as 1 minute. To the contrary, the placement of a single lead for His pacing may take 30 minutes or more, frequently without success. In those cases, the physicians typically revert to conventional lead placement at anatomy sites other than the bundle of His.

Another difficulty in implanting a His pacing lead concerns removal of the delivery device without disturbing the fixation of the pacing lead to the cardiac tissue. In order to prevent the helix of the pacing lead from becoming dislodged from the cardiac tissue, it is preferable to apply some forward force or pressure on the lead as the delivery sheath is gradually retracted. This complicates the sheath removal process and becomes more difficult to do as the partially retracted delivery sheath makes accessing the pacing lead difficult.

There therefore is a need for improvements to the devices used to deliver and implant electrode leads to make it easier to locate the bundle of His, to accurately implant an electrode therein, and to remove the delivery device once implantation has been completed.

BRIEF SUMMARY OF THE INVENTION

One aspect of the present invention provides a delivery device for delivering a pacing lead to the His bundle of a patient's heart. The delivery device includes a handle; an elongated sheath having a proximal end connected to the handle and a distal end remote from the handle, a distal portion of the sheath having a plurality of flexible sections spaced from one another along a length of the sheath, the sheath having a longitudinal rib extending from the proximal end to the distal end and being splittable along a first split line from the proximal end to the distal end; a pull wire having a distal end connected to the sheath distal to the flexible sections and extending to a proximal end; and a plurality of mapping electrodes positioned on the distal end of the sheath.

Another aspect of the present invention provides a method for delivering a pacing lead to the His bundle of a patient's heart. The method includes providing a delivery device having a sheath with a proximal end, a distal end, a longitudinal rib extending from the proximal end to the distal end, an axial lumen and a distal end face; inserting the sheath into the patient's body through the superior vena cava until a distal end portion of the sheath is positioned in the right atrium of the patient; inserting a pacing lead into the axial lumen of the sheath; deflecting the distal end portion of the sheath so that the distal end face of the sheath confronts the wall of the right atrium; moving the distal end face of the sheath relative to the wall of the right atrium until electrodes on the distal end face of the sheath receive electrical signals from the His bundle; fixing the pacing lead to tissue at the His bundle; and splitting the sheath along a split line from the proximal end to the distal end to remove the sheath from the pacing lead.

BRIEF DESCRIPTION OF THE DRAWINGS

Various embodiments of the present lead delivery device and methods for making and using the same are disclosed herein with reference to the drawings, wherein

FIG. 3 is a diagrammatic view showing the use of a prior art delivery device to locate and implant a pacing lead near the bundle of His;

FIGS. 7A-7K are transverse cross-sectional views of various embodiments of the delivery device sheath;

FIG. 23 is a diagrammatic view showing the use of the delivery device of FIG. 4 to locate and implant a pacing lead in the bundle of His.

DETAILED DESCRIPTION

As used herein, the terms "proximal" and "distal," when used in reference to a delivery device, are to be taken as relative to a user of the delivery device. "Proximal" is to be understood as relatively close to the user and "distal" is to be understood as relatively far away from the user. As used herein, the terms "substantially," "generally," and "about" are intended to mean that slight deviations from absolute are included within the scope of the term so modified.

Figure 1:
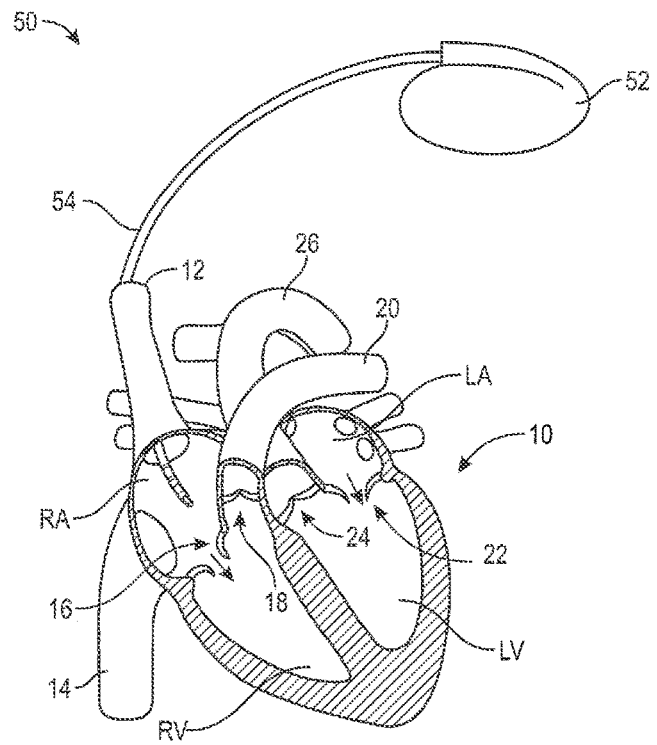
FIG. 1 is a highly schematic cutaway view of the heart illustrating an implantable cardiac pacing system.

FIG. 1 is a highly schematic cutaway view of heart 10 illustrating the right atrium RA, the right ventricle RV, the left atrium LA, and the left ventricle LV. During normal operation of heart 10, deoxygenated blood from the body is returned to the right atrium RA from the superior vena cava 12 and inferior vena cava 14. The right atrium pumps the blood through the atrioventricular or tricuspid valve 16 to the right ventricle RV, which then pumps the blood through the pulmonary valve 18 and the pulmonary artery 20 to the lungs for reoxygenation and removal of carbon dioxide. The newly oxygenated blood from the lungs is transported to the left atrium LA, which pumps the blood through the mitral valve 22 to the left ventricle LV. The left ventricle LV pumps the blood through the aortic valve 24 and the aorta 26 throughout the body.

Figure 2:
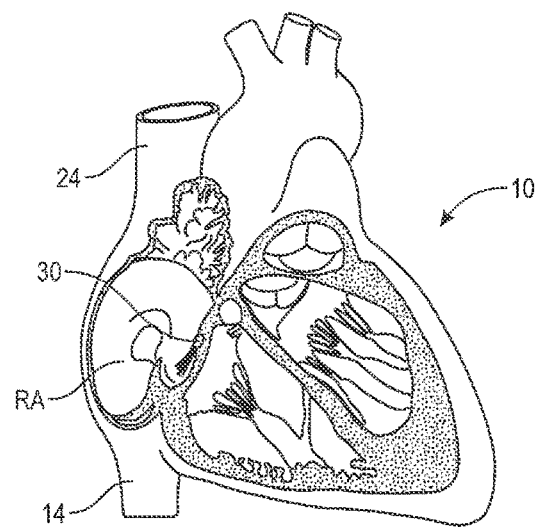
FIG. 2 is a highly schematic cutaway view of the heart showing the position of the bundle of His relative to other cardiac structures.

FIG. 2 is another schematic cutaway view showing the location of the bundle of His 30 in the heart. The bundle 30 consists of fast-conducting muscle fibers that begin at the atrioventricular node in the right atrium and pass to the interventricular septum. The bundle 30 divides in the septum into a right branch that travels along the right side of the septum and supplies excitation to the right ventricle, and a pair of left branches that travel along the left side of the septum and supply excitation to the left ventricle. The fibers in the branches terminate in an extensive network of Purkinje fibers which distribute excitation pulses to the layer of cells beneath the endocardium.

Returning to FIG. 1, also shown is a schematic view of a prior art His bundle mapping and pacing system 50. System 50 includes a subcutaneously disposed stimulation device or pacemaker 52 coupled to a pulsing lead 54 designed to penetrate the endocardium in contact with His bundle 30. Lead 54 enters the vascular system through one of several possible vascular access sites and extends through the superior vena cava 12 to the right atrium RA.

FIG. 3 is a diagrammatic view showing the use of lead 54 to locate the bundle of His 30. While it is being maneuvered through the patient's vasculature to the right atrium RA, lead 54 is held within a protective sheath 56. In a conventional system, sheath 56 may have a fixed curve that approximates the position of the bundle of His relative to the superior vena cava 12. Once sheath 56 is in the right atrium, the tip of lead 54 is advanced out from the sheath to expose electrodes 60 and 62 and helical fixation anchor 64. Electrodes 60 and 62 may be spaced apart on lead 54 by up to about 10 mm. Sheath 56 may be manipulated to advance lead 54 parallel to the atrial wall until the faint electrical signals from His bundle 30 are identified. This typically occurs when electrodes 60 and 62 are on opposite sides of the bundle, as depicted in FIG. 3. At this point, sheath 56 may be manipulated to implant fixation anchor 64 in the atrial wall. However, as fixation anchor 64 is distal to electrodes 60 and 62, when the electrodes detect the bundle of His 30, the fixation anchor is at a position spaced several millimeters from the bundle. Hence, if implanted at this location, fixation anchor 64 and lead electrodes 60 and 62 will be offset from the bundle of His, such that any pacing pulses from pacemaker 52 may not stimulate and pace the His bundle.

Figure 4:
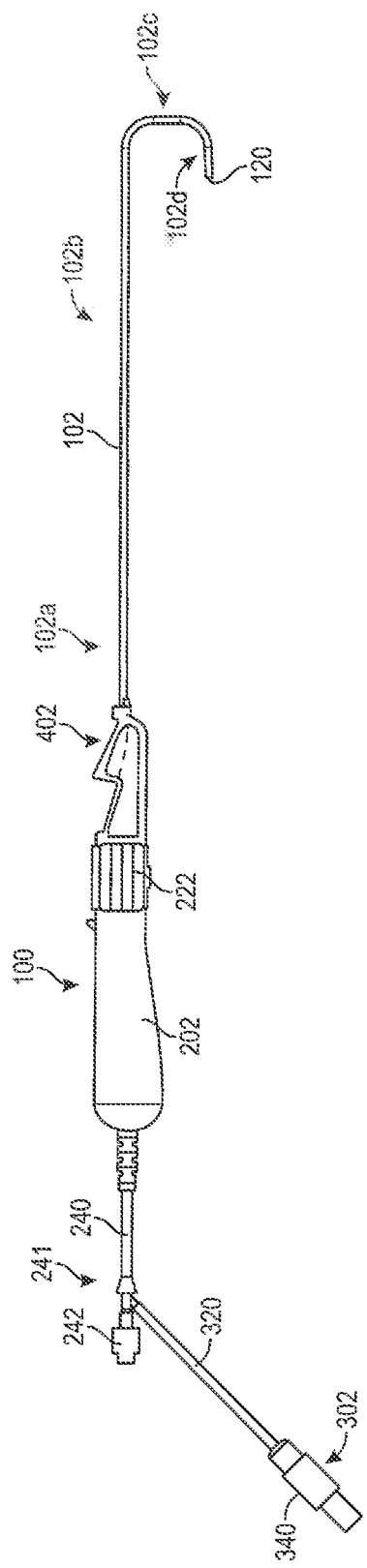
FIG. 4 is a side view of a pacing lead delivery device according to the present disclosure.

The present disclosure is directed to a special lead delivery device configured to address the foregoing difficulties in locating and implanting a lead electrode in the bundle of His 30, and to a sheath construction that facilitates removal of the sheath once the lead electrode has been implanted. One embodiment of a delivery device 100 according to the present disclosure is shown in FIG. 4. Delivery device 100 includes four major components or assemblies, including a sheath 102, a handle 202, a connector assembly 302, and a fluid flushing assembly 241. Connector assembly 302 typically comprises an electrical connector 340 disposed near handle 202 and provides electrical connection from the connector 340 to electrodes 310, 312 and to optional electrode 350 (FIG. 5B) mounted on the outer surface of sheath 102 near its distal end, via conductive wires 312 (FIG. 5B) embedded within the sheath. Connector assembly 302 is electrically linked to an external electrogram mapping system. Handle 202 contains a hemostasis hub 402 for accepting and tethering to the proximal portion of sheath 102 and includes a mechanism for deflecting the distal end of the sheath. Sheath 102 has a central opening or lumen through which a pacing lead, via the entrance to hemostasis hub 402, is introduced and advanced distally. Fluid flushing assembly 241 is arranged to connect to hemostasis hub 402 leading to the center lumen of sheath 102. Each of sheath 102, handle 202, hemostasis hub 402, and connector assembly 302, etc. is described in more detail below.

Figure 5A:
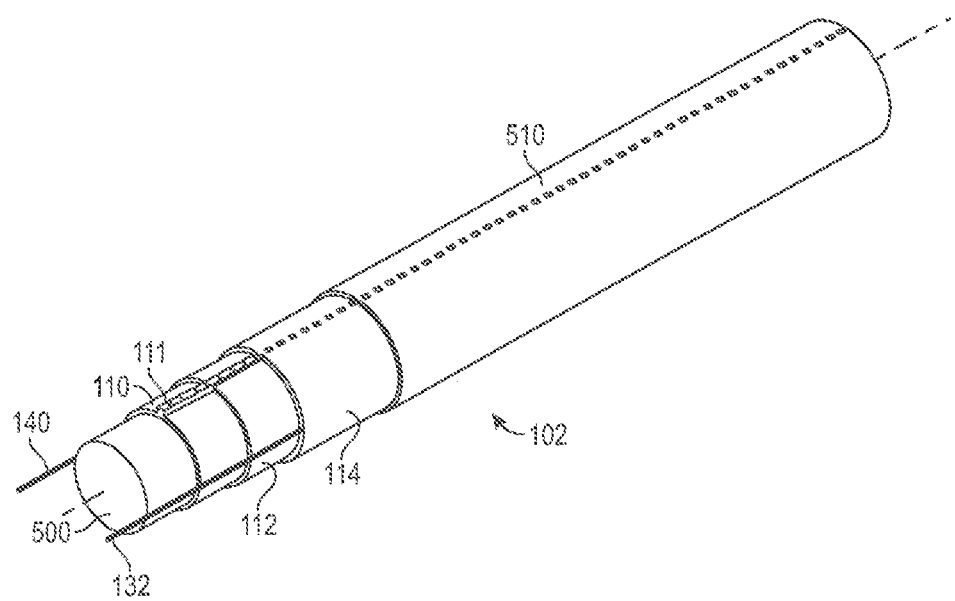
FIG. 5A is a perspective view showing the layers of the delivery device sheath and the components used in assembling the sheath.
Figure 5B:
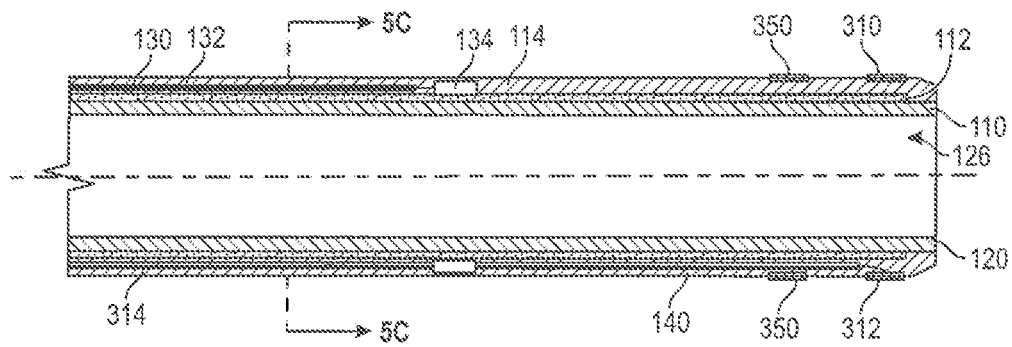
FIG. 5B is a longitudinal cross-section of the distal portion of the delivery device sheath.
Figure 5C:
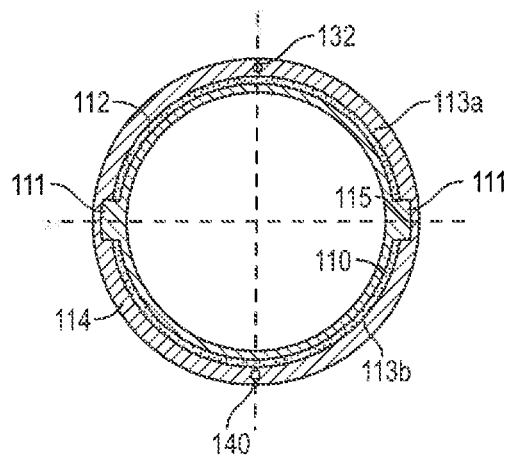
FIG. 5C is a transverse cross-sectional view of the delivery device sheath taken along line 5C-5C of FIG. 5B.
Figure 6:
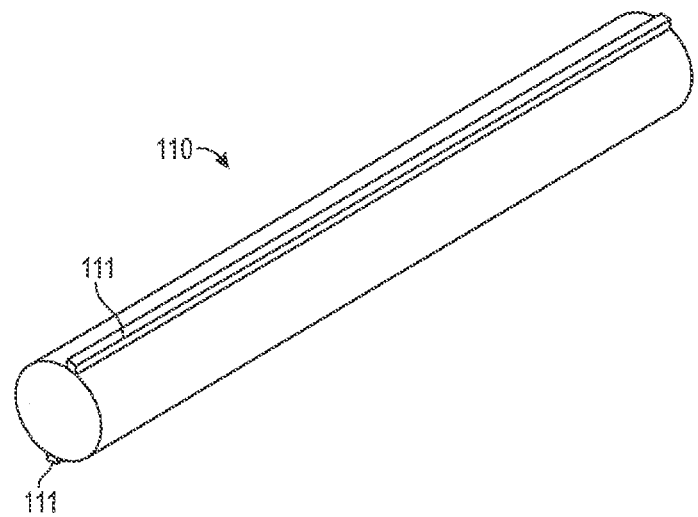
FIG. 6 is a perspective view of the inner layer or liner of the delivery device sheath shown in FIG. 5A.

Sheath 102 may consist of four sheath sections, including a proximal section 102*a*, a body section 102*b*, a deflectable section 102*c* and a distal end section 102*d* with an atraumatic distal tip 120. The structure and configuration of sheath 102 are designed to reliably introduce a pacing lead into a patient's heart, while exhibiting a high degree of maneuverability as provided by the ability to deflect its deflectable section 102*c*. It is therefore desirable that sheath 102 have a sufficient degree of columnar strength for advancement through the tortuous vasculature of the patient, and sufficient kink resistance to bend smoothly. Sheath 102 achieves these characteristics from a multi-layer construction as shown in FIGS. 5A-5C. An inner layer 110 or liner of sheath 102 may be formed from a tube of a lubricious material to facilitate the passage of a pacing lead through the sheath, as well as the rotation of the lead within the sheath as it is being fixed to heart tissue. One lubricious material for forming liner 110 may be polytetrafluoroethylene (PTFE). Liner 110 includes at least one rib or wedge 111 that protrudes radially from the outer surface of the liner from the proximal end to the distal end of sheath 102. In a preferred arrangement, liner 110 may include two such ribs 111 that extend substantially parallel to one another on diametrically opposed surfaces of the liner. Although ribs 111 are shown as having a square or rectangular cross-section in FIG. 5C, other configurations are possible as will be described further below in connection with FIGS. 7A-7F.

The liner 110 may be formed from a free-flowing fine powder form of PTFE mixed with a lubricant, such as a hydrocarbon fluid, including, but not limited to, Naphtha solvents, $C_9$-$C_{15}$ hydrocarbons or isoparaffinic hydrocarbons, or mineral spirits to create a paste. One or more particulate ingredients may be added to the paste, including radiopaque fillers, such as barium sulfate, inorganic pigments, and/or reinforcing nanoclay particles. The paste may be compression-molded into a preform of an appropriate shape, such as a hollow or solid cylinder. The preform may then be formed into tubular liner 110 using a paste or ram extrusion process. Following extrusion, liner 110 may be subjected to a series of processing ovens at sequentially increasing temperatures to flash off the lubricants and to partially or completely sinter (or thermally fuse) the PTFE powder particles. By ram extruding the PTFE paste at high pressures, the PTFE powder particles will form platelet-like fibrils oriented in the axial or extrusion direction. Because of weak intermolecular forces between the oriented fibril platelets, liner 110 exhibits excellent peelability in its length direction.

PTFE materials exhibit a high degree of chemical inertness and hydrophobicity, and therefore do not readily adhere to other polymers. In order to integrate liner 110 with the other layers of sheath 102, the outer surface of liner 110 may be chemically activated through physical and/or chemical surface treatment methods, including chemical plasma treatment or chemical etching processes known in the art. In one such process, a fluorocarbon etchant containing sodium naphthalene may be utilized to chemically treat the outer surface of liner 110 through a series of process steps, including an etching step, several rinsing steps and a drying step. In the etching step, liner 110 may be immersed in the etchant at a temperature of between about 55° C. and about 65° C. in a tight vessel with nitrogen purging for a duration of between about 30 seconds and a few minutes. Light agitation of the etchant may help promote the etching effect. Following the etching step, the etchant may be drained from the vessel and liner 110 may be subjected to a series of successive rinsing steps, each at a temperature of about 70° C. In the first rinsing step, liner 110 is immersed in an alcohol bath (containing, for example, between about 75 wt % and about 90 wt % isopropanol or methanol) for between about 5 seconds and about 20 seconds. The alcohol chemically deactivates and partially dissolves sodium naphthalene. In the second rinsing step, liner 110 is immersed in chlorine-free carbon-filtered, distilled or deionized water for between about 15 seconds and about 30 seconds. The second rinsing step may be followed by a third rinsing step in which liner 110 is immersed in an acidic water bath (containing between about 2 wt % and about 5 wt % acidic acid) for about 60 seconds. The pH of the acidic water bath should be between about 4 and about 6. The acidity of the bath neutralizes the alkalinity of the etchant and produces a faster and more thorough cleaning effect. Following the rinsing steps, liner 110 may be dried, for example using forced hot air or an oven at between about 70° C. and about 80° C. until fully dried. During the chemical etching of liner 110, the inner lumen thereof should be sealed off or otherwise protected so as to maintain its inherent surface lubricity.

Sheath 102 may comprise a braided layer 112 disposed over liner 110 to enhance its columnar and torsional strengths. Braided layer 112 may include a plurality of metallic braids impregnated with one or more thermoplastic polymers. Examples of acceptable thermoplastic polymers include polyamides, such as nylon 11, nylon 12, nylon 612, and the like; polyesters, such as poly(butylene terephthalate), poly(ethylene terephthalate), and the like; and thermoplastic elastomers, such as poly(ether-block-amide) copolymer resins, poly(ether-co-ester) block copolymer resins, and various thermoplastic polyurethane block copolymer resins. The thermoplastic polyurethane block copolymer resins can have different hard and soft segment chemistries, including, but not limited to, polyether-based aromatic or aliphatic polyurethanes, polyester-based aromatic or aliphatic polyurethanes, polycarbonate-based aromatic and aliphatic polyurethanes, silicone-containing polyether-based aromatic or aliphatic polyurethanes, silicone-containing polycarbonate-based aromatic or aliphatic polyurethanes, or any combinations thereof. Braided layer 112 may include two C-shaped sections 113*a* and 113*b*, with one section positionable on each side of ribs 111. Sections 113*a* and 113*b* may extend along the entire length of sheath 102 or may extend only through the proximal section 102*a* and body section 102*b* of the sheath.

In one method for forming braided layer 112, a first one of the aforementioned thermoplastic polymers may be extruded onto a mandrel whose outer diameter is approximately equal to the lumen diameter of liner 110 to form an inner jacket layer. Multi-thread metallic wires may then be braided over the inner jacket layer. The wires may be round, with diameters of from about 0.02 mm to about 0.2 mm, or flat, with sizes ranging from about 0.01 mm thick by about 0.05 mm wide to about 0.1 mm thick by about 0.20 mm wide. The braid may be woven with a regular, full-load pattern (with one wire passing under two wires and then over two wires), a diamond pattern (with two side-by-side wires alternately passing under two side-by-side wires then over two side-by-side wires), a half-load diamond pattern (with one wire passing under one wire and then over one wire) or other patterns known in the art.

Following the braiding step, another of the aforementioned thermoplastic polymers may be extruded over the braids to form an outer jacket layer. The thermoplastic polymers forming the inner and outer jacket layers may be the same, similar or different. However, they should be chemically compatible or miscible so that the polymer of the outer jacket layer strongly adheres to the polymer of the inner jacket layer as it is extruded thereover. This strong adherence may be achieved by using a polymer with a relatively lower melt temperature for the inner jacket layer and a polymer with a relatively higher melt temperature for the outer jacket layer. As a result, the polymer of the outer jacket layer will thermally fuse and strongly adhere to the polymer of the inner jacket layer, embedding the metallic braids therebetween. Once braided layer 112 has been formed or pre-made, it may be split in half in the longitudinal direction using a cutting fixture to form symmetrical C-shaped sections 113a and 113b.

Figure 8:
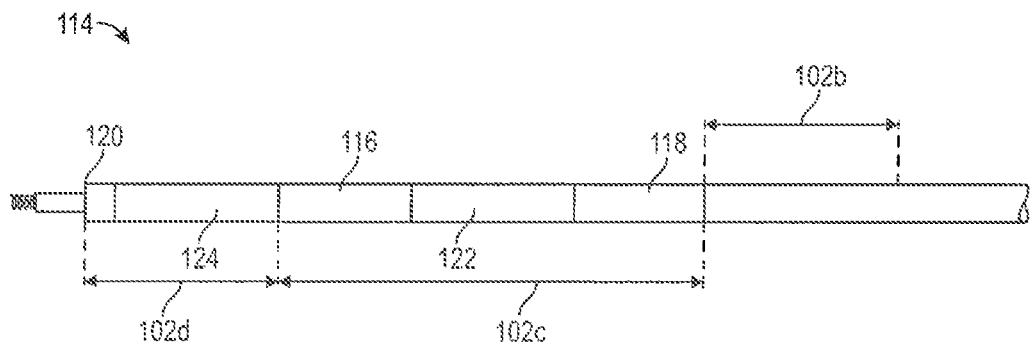
FIG. 8 is an enlarged view of the distal end of the delivery device sheath.

Sheath 102 further includes an outer polymer layer 114 disposed over the C-shaped sections 113a and 113b of braided layer 112. Outer layer 114 extends along the whole length of sheath 102 and preferably provides sufficient columnar strength in the proximal section 102a and body section 102b of sheath 112 and excellent material flexibility in the deflectable section 102c as well as material aromaticity in the distal end section 102d of the sheath. Layer 114 may be formed from different polymers capable of being extruded to the desired dimensions and of providing varied material stiffnesses or flexibilities as desired, including any of the thermoplastic polymers described above for forming braided layer 112. Exemplary materials for forming outer layer 114 include various chemically similar, but mechanically different, polymer materials based on a family of poly(ether block amide) copolymer resins sold under the trade name Pebax® by Arkema Inc. Alternatively, polymer materials used for making outer layer 114 may include other chemically similar, but mechanically different, polymer materials based on a family of thermoplastic polyurethane resins sold under the trade name Pellethane® by Lubrizol Corporation. For the proximal section 102a and body section 102b of sheath 102, outer layer 114 may be formed from a tube of a Pebax® or Pellethane® polymer having a hardness of at least about Shore D55, preferably from a Pebax® or Pellethane® polymer having a hardness of about Shore D60 to about D80, and more preferably from a Pebax® or Pellethane® polymer having a hardness of about Shore D70 to about D75. For the deflectable section 102c of sheath 102, shown more clearly in FIG. 8, outer layer 114 includes three sections 116, 118, and 122. Two sections 116 and 118 of outer layer 114 are made of a less hard, and therefore more pliable, material than the other section 122.

Sections 116 and 118 may also be formed from tubes of Pebax® poly(ether block amide) or another Pellethane® thermoplastic polyurethane elastomer, but with a hardness of between about Shore D20 and about Shore D40, preferably about Shore D35. Sections 116 and 118 each may have a length in the axial direction of sheath 102 of between about 1 cm and about 3 cm. In a preferred arrangement, each of sections 116 and 118 may have a length in the axial direction of sheath 102 of between about 1.5 cm and about 2 cm. Section 116 may be spaced from the distal tip 120 of sheath 102 by between about 1 cm and about 3 cm, preferably by between about 1.5 cm and about 2.5 cm. Section 118 may be spaced from section 116 by between about 0.5 cm and about 2 cm, preferably by between about 1 cm and about 2 cm. Section 122 of outer layer 114 between sections 116 and 118, and the distal section 124 of outer layer 114 (positioned in distal end section 102d of sheath 102) are preferably made from the same relatively rigid material as is used to form the outer later in the proximal section 102a and body section 102b of the sheath. Sections 116 and 118 may be joined to the other sections of layer 114 by gluing, ultrasonic welding, reflow heating or other known techniques. In a preferred arrangement, the distal tip 120 of sheath 102 may be formed from Pebax® or another polymer that is softer than the material forming the distal section 124 of outer layer 114 so as to provide an atraumatic tip to the sheath. In some embodiments, the polymers forming outer layer 114 may include radiopaque fillers, such as barium sulfate, tungsten, bismuth trioxide, bismuth subcarbonate, bismuth oxychloride and the like. Polymers containing a radiopaque filler may be used for outer layer 114 in different sections of sheath 102.

Despite the fact that different sections of outer layer 114 may be formed from different materials, the polymers forming the different sections may first be extruded as continuous tubes and then cut to lengths. Depending on the cross-sectional configuration of sheath 102, as shown in FIGS. 5C and 7A-K, the sections of outer layer 114 may be slit in the longitudinal direction to form symmetrical C-shaped sections. Where outer layer 114 is to be assembled to sheath 102 in a tubular form without slitting, as in FIG. 5C, the outer layer is preferably extruded with one or more inner recesses 115 that correspond in shape and size to the ribs 111 on liner 110.

A lumen 126 (FIG. 5B) extends continuously through sheath 102 along its entire length. Lumen 126 has a diameter that is slightly larger than the diameter of the pacing lead to be delivered to the heart by delivery device 100. For example, for a 7 French pacing lead (having a diameter of about 2.33 mm), lumen 126 may have a size of about 7.5 French (a diameter of about 2.5 mm).

A pull wire 130 may extend through a narrow tube 132 extending along the length of sheath 102 between braided layer 112 and outer layer 114. In an alternate arrangement, tube 132 may be positioned between liner 110 and braided layer 112. Tube 132 is preferably formed from a material that will resist collapsing or kinking during the manufacture of sheath 102 and the use of delivery device 100. Materials appropriate for forming tube 132 include polyetherimide, polyimide, PTFE or other high temperature polymers. Optionally, tube 132 may include metal braids to further enhance its kink resistance. Pull wire 130 may be welded or otherwise affixed at its distal end to a pull wire ring 134 and may be connected at its proximal end to an operating mechanism in handle 202, described more fully below. Pull wire ring 134 is axially located in the distal end section 102d of sheath 102 and is fixed in place between braided layer 112 and outer layer 114 or between liner 110 and braided layer 112. Although referred to as a "ring," pull wire ring 134 may actually consist of one C-shaped section that may be positioned on one side of ribs 111, or two C-shaped sections that are not connected to one another, but that may be positioned on opposite sides of ribs 111. As sheath 102 need only be deflected in a single direction, a single C-shaped section may be positioned on the side of the sheath toward which deflectable section 102c is to be deflected. Tube 132 for pull wire 130 would be positioned on the same side of sheath 102 as the C-shaped portion of pull wire ring 134.

Figure 9A:
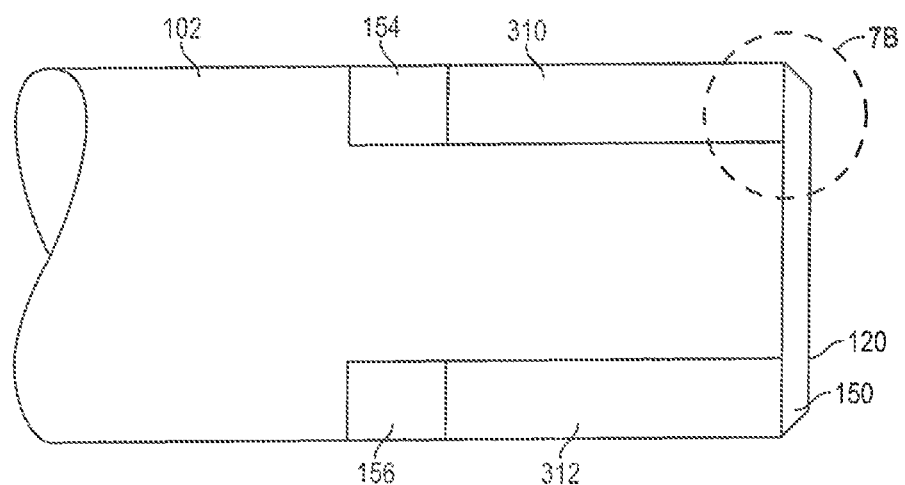
FIG. 9A is an enlarged side view of the distal tip of the delivery device sheath showing the positions of the mapping electrodes thereon.

The distal end section 102d of sheath 102 also includes a pair of split mapping electrodes 310 and 312, as shown in FIGS. 5B and 9A. Electrodes 310 and 312 are electrically connected to connector assembly 302 via electrical conductor 314, and they may be identical to one another. Any appropriate metal, such as platinum-iridium, may be used to form electrodes 310 and 312, and they may be diametrically opposed to one another on opposite sides of sheath 102. For a sheath having a conventional size, the ends of electrode 310 may be spaced apart in the circumferential direction from the ends of electrode 312 by between about 1 mm and about 3 mm, preferably by about 2.5 mm. An electrical conductor 314 may extend from each of electrodes 310 and 312 through a narrow tube 140 extending along the length of sheath 102 between braided layer 112 and outer layer 114 or between liner 110 and braided layer 112. Tube 140 may be formed from the same polymer used to form tube 132 and may optionally include metal braids to enhance its kink resistance. Upon exiting tube 140, conductors 314 may travel through a lumen (not shown) in handle 202 and through a conduit 320 to an electrical connector 340 (FIG. 4). As will be explained further below, electrodes 310 and 312 are preferably positioned at the distal tip 120 of sheath 102, or very close to the distal tip, and on opposite sides of ribs 111.

The fabrication of sheath 102 will now be described with reference to FIGS. 5A to 5C. To fabricate sheath 102, its individual components may be sequentially assembled over a supporting core rod 500. Thus, after treatment of its outer surface, liner 110 may be assembled over core rod 500, followed by sections 113a and 113b of braided layer 112 on either side of ribs 111. Pull wire ring 134 (i.e., at least one C-shaped section thereof) may then be positioned over braided layer 112 in the distal end section 102d of sheath 102, and tube 132 containing pull wire 130 that has been pre-welded to the pull wire ring may be positioned alongside the braided layer. Alternatively, tube 132 may be positioned against liner 110 and sections 113a and 113b of braided layer 112 may be assembled thereover. Pull wire 130 extends from pull wire ring 134 through tube 132 and out from the proximal end thereof. Similarly, tube 140 is properly positioned, and electrical conductors 314 may be threaded through tube 140 and out from the proximal end thereof. As will be appreciated from the discussion below, a C-shaped section of pull wire ring 134, tube 132 and pull wire 130 preferably are positioned along the side of braided layer 112 toward which sheath 102 is to be deflected. Tube 140 and electrical conductors 314 may be positioned on the side of braided layer 112 diametrically opposed to tube 132 or at another position around the circumference of the braided layer. However, neither tube 132 nor tube 140 should be positioned in close proximity to a rib 111 as such positioning could interfere with the peelability of sheath 102. The sections of outer layer 114 corresponding to the different sections of sheath 102, including proximal section 102a, body section 102b, deflectable section 102c (namely sections 116, 118, and 122 of outer layer 114), and distal end section 102d (namely section 124 of outer layer 114) with distal tip 120, may then be assembled over the previously assembled components. Depending on the cross-sectional configuration of sheath 102, the sections of outer layer 114 may be assembled to the other components either as sections of full tubes or as C-shaped tube sections. When all of the individual components of sheath 102 have been assembled together and their relative positions have been properly adjusted, a heat-shrinkable tube 510 may be applied thereover to fully encapsulate the assembly. When heated in a reflow process to an appropriate thermal lamination temperature near or above the critical thermal transition temperatures of the polymers used for braided layer 112 and outer polymer layer 114, the polymers in those layers will partially or completely melt, thermally bonding the layers to one another and to liner 110. Liner 110, on the other hand, will not melt, so that its axially oriented platelet-like fibrils will remain intact. However, the chemical etching of the outer surface of liner 110 will cause the polymers of braided layer 112 to strongly adhere to it.

Although braided layer 112 was described above as including metal braids imbedded in inner and outer polymer jacket layers, that may not be the case. In an alternate embodiment, braided layer 112 may be formed simply by forming the metal braids on a disposable mandrel without the polymer jacket layers. The metal braids may be formed into a tubular shape and assembled to the other sheath components in the tubular form or may be cut longitudinally to form two C-shaped sections. In either arrangement, the individual components of sheath 102 would be assembled as described above. That is, the metal braided layer 112 would be assembled over liner 110 (and over or under tubes 132 and 140), pull wire 130, pull wire ring 134, electrodes 310 and 312, conductors 314, and relevant constraining tubes 132 and 140 would be properly positioned, and then the sections of outer layer 114 would be assembled thereover. During the subsequent reflow process, the polymers of outer layer 114 will melt, permeate the metal braids and thermally fuse to bond with liner 110.

As electrodes 310 and 312 are split mapping electrodes that do not fully circumscribe sheath 102, the electrodes must be strongly attached to the sheath so as to not become detached therefrom upon advancement of the sheath through the patient's vasculature to deliver a pacing lead to the bundle of His 30 or during removal of the sheath from the patient following such procedure. Thus, while electrodes 310 and 312 may be positioned at the tip of sheath 102 to thereby be exposed on the distal end face of the sheath, the electrodes are preferably spaced from the tip of the sheath so as to be surrounded on all sides by a continuous mass of the sheath polymer.

Figure 9B:
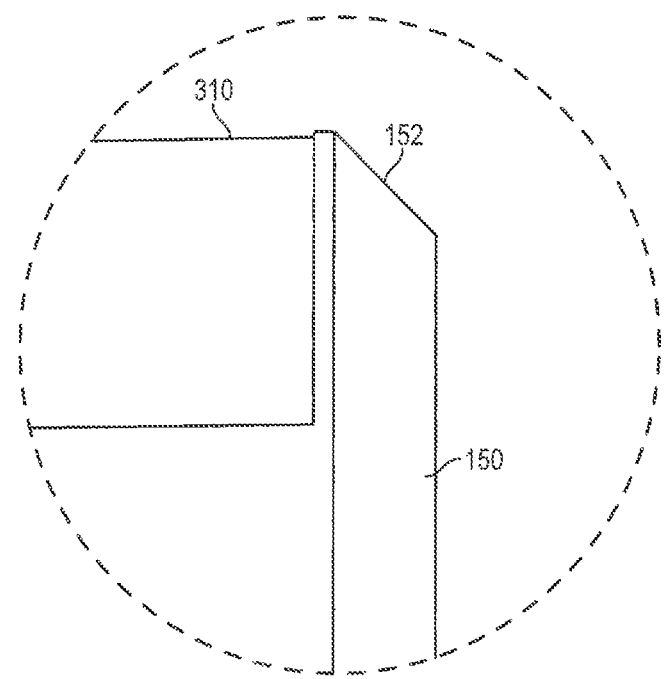
FIG. 9B is an enlarged view of a portion of FIG. 9A.
Figure 9C:
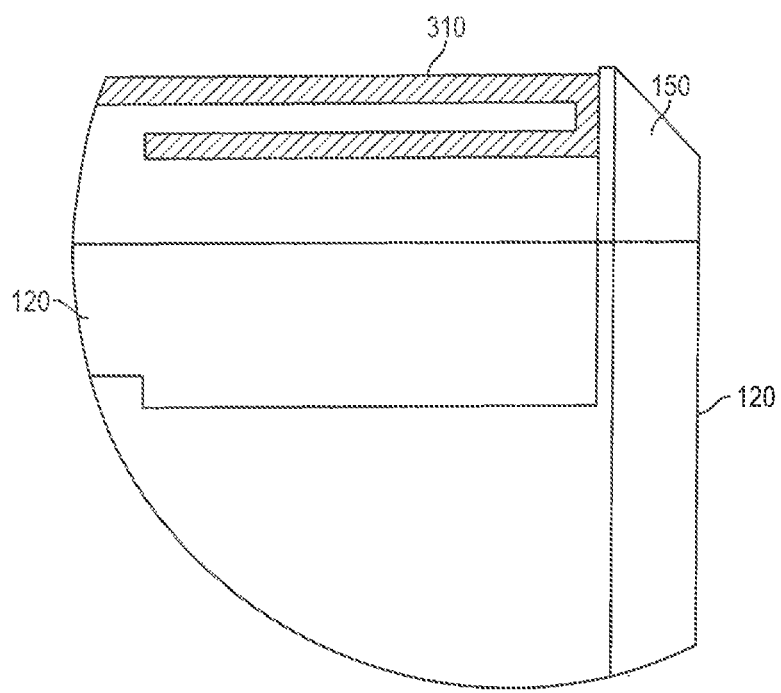
FIG. 9C is a highly schematic enlarged longitudinal cross-section of the illustration shown in FIG. 9B.
Figure 10:
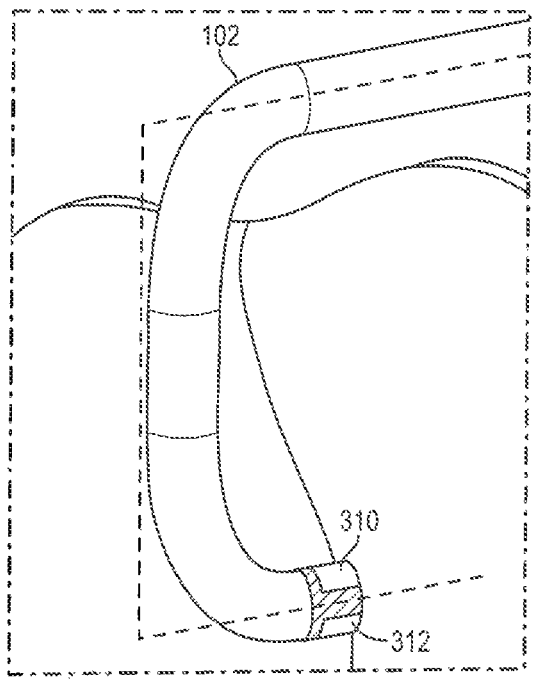
FIG. 10 is an enlarged view of the distal end of the delivery device sheath in a deflected condition.

FIGS. 9A-C illustrate the positions of electrodes 310 and 312 at the distal tip 120 of sheath 102. The positions of electrodes 310 and 312 on sheath 102 are based generally on two considerations—obtaining the strongest signal from the bundle of His and assuring the adherence of the electrodes to the sheath. As noted, it is preferable to space electrodes 310 and 312 from the tip of sheath 102 to more securely adhere the electrodes to the sheath. However, the ability of the electrodes to sense signals from the bundle of His is greatest when the electrodes are exposed on the distal end face of the sheath. As a compromise, it is preferable to position the electrodes as close as possible to the distal end face of sheath 102 while still allowing a region 150 of polymer between the electrodes and the tip of the sheath. In one embodiment, recessing the electrodes about 0.5 mm from the tip of sheath 102 is preferred. In addition to more securely fixing the electrodes to sheath 102, spacing the electrodes proximally of the distal tip of the sheath keeps sharp edges of the electrodes from being exposed, thereby reducing trauma to tissue as delivery device 100 is advanced through the patient's vasculature. As shown in FIG. 9B, the tip of sheath 102 also may be chamfered, as at 152, further reducing trauma during the advancement of delivery device 100. Making the distal end of sheath 102 black or another dark color, as shown in FIG. 10, will highlight metallic electrodes 310 and 312 and make them more visible.

Another consideration in where to position electrodes 310 and 312 on sheath 102 has to do with the direction in which the distal tip of the sheath deflects. In that regard, it is preferable to position the electrodes on sheath 102 so that, when the sheath is deflected, the electrodes are generally aligned in the direction in which the fibers of the bundle of His are oriented. The maximum signal will be detected from the bundle of His when both electrode 310 and electrode 312 are located directly thereover. Thus, if electrodes 310 and 312 are oriented on sheath 102 on opposite sides of the deflection plane defined by the deflected distal tip of the sheath (i.e., at positions located 90° from the positions shown in FIG. 10), only one electrode at a time will be able to be located over the bundle of His 30. As sheath 102 is moved relative to the atrial septal wall in an area in close proximity to the His bundle, one electrode may move closer to the His bundle while the other electrode may move away from the His bundle, such that the maximum possible signal will not be obtained. On the other hand, by positioning both of electrodes 310 and 312 in the deflection plane, shown in dashed lines in FIG. 10, both electrodes can lie over the bundle of His 30 at the same time. In fact, as sheath 102 is moved across the atrial septal wall, there will be a distance equal to about the diameter of the sheath within which the maximum His bundle signal can be detected.

In order to assemble electrodes 310 and 312 to sheath 102, a portion of the polymer is first removed from areas on opposite sides of the distal end of the sheath, creating cavities 154 and 156 sized to receive the electrodes. Cavities 154 and 156 may be formed either before or after assembling the components of sheath 102. In one example, the polymer may be removed by laser ablation, although other removal techniques known in the art may also be employed, including but not limited to cutting, grinding, chemical etching and the like. Preferably, the polymer is removed to a depth that is substantially the same as the radial thickness of electrodes 310 and 312 so that, once assembled to sheath 102, the outer surface of the electrodes will be substantially flush with the outer surface of the sheath. After a conductor 314 has been assembled to each of electrodes 310 and 312, the electrodes are inserted into cavities 154 and 156, respectively, and the distal end of the sheath may again be subjected to a reflow heating process to partially or completely melt the outer polymer of braided layer 112 and outer polymer layer 114 to mechanically interlock the electrodes with the sheath's polymer material. FIG. 9C is a cross-sectional view showing electrode 310 embedded within the polymer at the distal end of sheath 102.

FIGS. 11-16 illustrate examples of structures for forming electrodes 310 and 312 to facilitate their secure assembly to sheath 102. Each of the curved structures shown in these figures may be laser cut or otherwise formed from a metal tube having a circumference that is substantially similar to the circumference of sheath 102 so that the curvature of the resultant electrodes matches that of the sheath. Structures not shown with a curved configuration may be formed flat from flat sheet stock and subsequently bent to have a curvature that matches the curvature of sheath 102.

Figure 11:
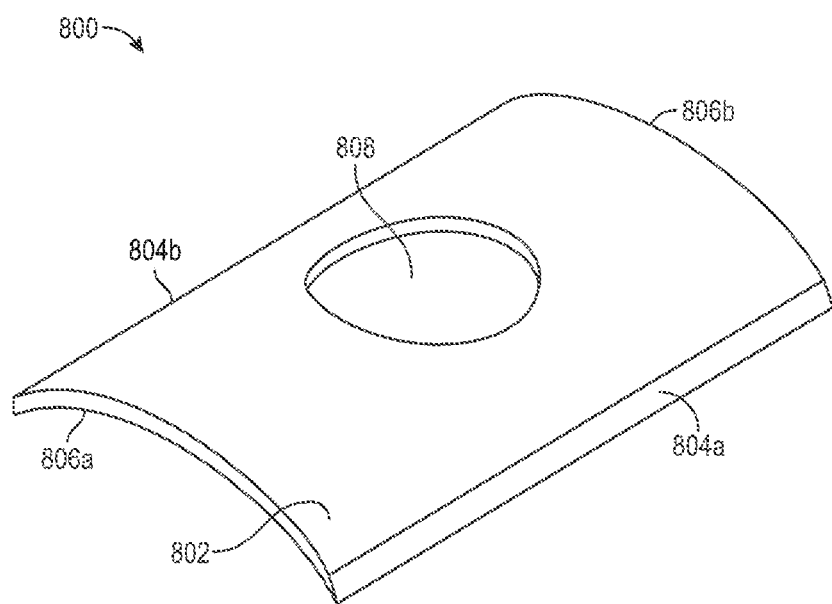
FIG. 11 is a perspective view of one embodiment of a sheath electrode.

The electrode 800 shown in FIG. 11 is generally in the form of a plate 802 having a curvature that is substantially similar to the curvature of the outer surface of sheath 102. The side edges 804a and 804b of plate 802 (i.e., the edges that are substantially parallel to the longitudinal axis of sheath 102) are beveled so that, during the reflow heating process, the softened or molten polymer can flow over the beveled edges to securely hold electrode 800 to the sheath. Rather than the side edges of plate 802 being beveled, electrode 800 may be formed so that the end edges 806a and 806b of plate 802 (i.e., the edges that are substantially orthogonal to the longitudinal axis of sheath 102) may be beveled, or both the side edges and end edges may be beveled. Plate 802 may optionally include an aperture 808 that may fill with polymer during the reflow heating process to further prevent electrode 800 from moving longitudinally relative to the sheath.

Figure 12:
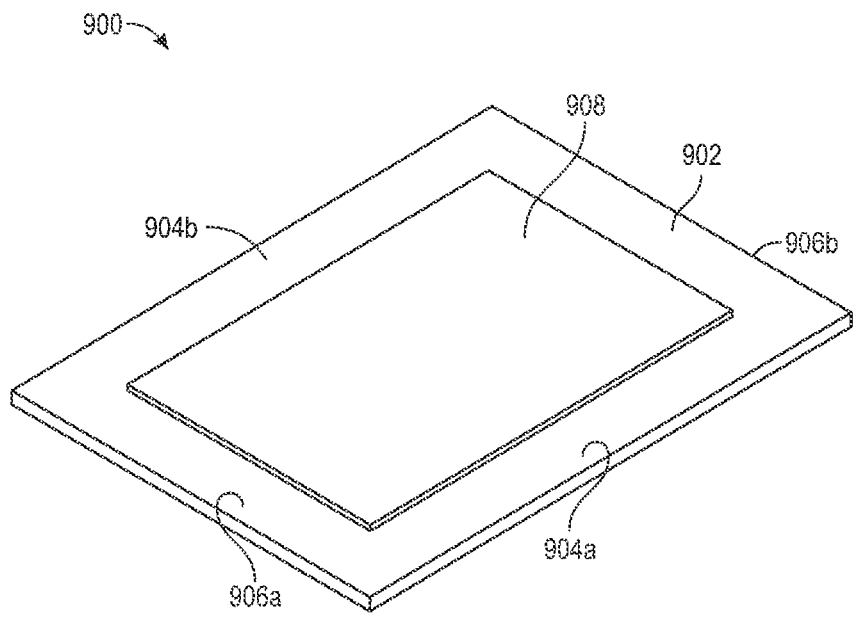
FIG. 12 is a perspective view of another embodiment of a sheath electrode.

In the embodiment shown in FIG. 12, a generally flat metal plate 902 may be formed with a reduced thickness along its side edges 904a and 904b and end edges 906a and 906b. This reduced thickness may be formed by a stamping operation, by grinding, machining or other mechanical technique, by chemical etching or by other known techniques. As a result, the thickness of the side and end edges of plate 902 may be less than the thickness of a center region 908. Once the edges of plate 902 have been thinned, the plate may be deformed into an electrode 900 having a curved shape that substantially matches the curvature of sheath 102. Following the attachment of conductors 314, an electrode 900 may be assembled in each of cavities 154 and 156 and the distal end section 102d of sheath 102 may be subjected to a reflow heating process. During such process, the softened or molten polymer will flow to cover the thinned edges of electrodes 900 to firmly hold same in place.

Figure 13:
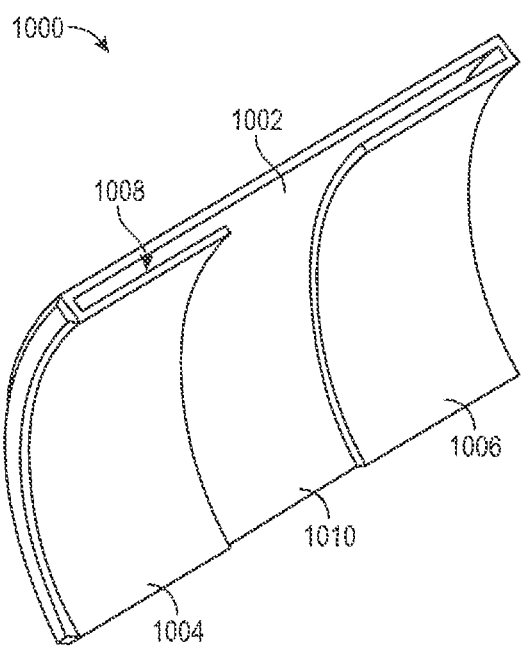
FIG. 13 is a perspective view of yet another embodiment of a sheath electrode.

FIG. 13 shows an electrode 1000 that is generally in the form of a rectangular plate 1002 having a curvature that is substantially similar to the curvature of the outer surface of sheath 102. The end portions 1004 and 1006 of plate 1002 are bent toward one another against the inner surface of plate 1002 as in a conventional staple so that a slight gap 1008 is formed between end portions 1004 and 1006 and the main body 1010 of the plate. Following the attachment of conductors 314, electrodes 1000 may be assembled in appropriate positions near the distal tip 120 of sheath 102 and the distal end section 102d of the sheath may be subjected to a reflow heating process. As the polymer of sheath 102 softens, electrodes 1000 may sink into the polymer, and the polymer may flow into the gaps 1008 between end portions 1004 and 1006 and main body 1010, securely affixing the electrode to the sheath. Thus, preforming cavities 154 and 156 in sheath 102 may not be necessary in this embodiment. While FIG. 13 shows end portions 1004 and 1006 bent at right angles to the sides of plate 1002, that need not be the case. End portions 1004 and 1006 may be bent at an angle other than right angles if it is desired to produce a non-rectangular electrode surface.

Figure 14:
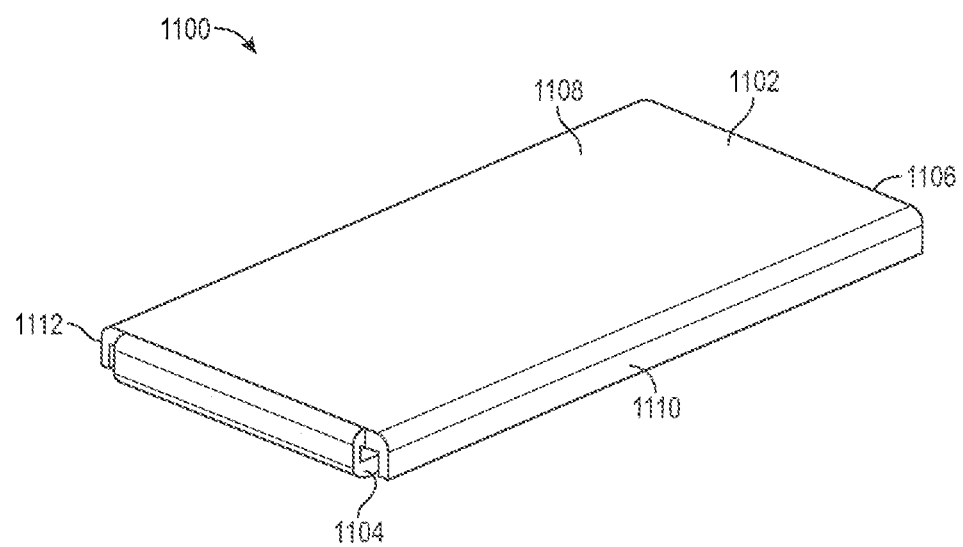
FIG. 14 is a perspective view of still a further embodiment of a sheath electrode.

FIG. 14 shows an electrode 1100 which is a variant of electrode 1000 shown in FIG. 13. The difference between the electrodes is that, in addition to main body 1108 and end portions 1104 and 1106, the plate 1102 of electrode 1100 includes projections 1110 and 1112 that protrude from the lateral sides of the main body. In addition to folding the end portions 1104 and 1106 of plate 1102 against the inner surface of the plate, projections 1110 and 1112 may be folded inwardly until they cover the side edges of the end portions. Relative to electrode 1000, electrode 1100 eliminates exposed sharp edges that could damage tissue and provides a more secure affixation of the electrode to sheath 102, particularly in the circumferential direction.

Figure 15A:
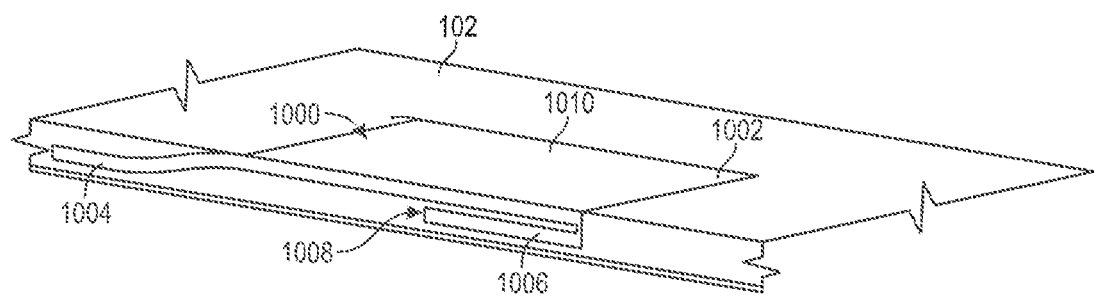
FIGS. 15A-D are highly schematic longitudinal cross-sections of the sheath electrode of FIG. 13 embedded in a sheath.

Different configurations for securing the electrode 1000 of FIG. 13 to sheath 102 are shown in the longitudinal cross-sectional views shown in FIGS. 15A-D. In each configuration, following the attachment of a conductor 314 to each electrode 1000, one electrode is placed into each of cavities 154 and 156 and the distal end section 102d of sheath 102 is subjected to a reflow heating process, locking the electrodes in place. Referring to FIG. 15A, rather than bending the end portions 1004 and 1006 of plate 1002 toward one another, end portion 1006 is bent toward the inner surface of plate 1002, while end portion 1004 is bent away from end portion 1006 and main body 1010 so that end portions 1004 and 1006 lie in substantially the same plane.

Figure 15B:
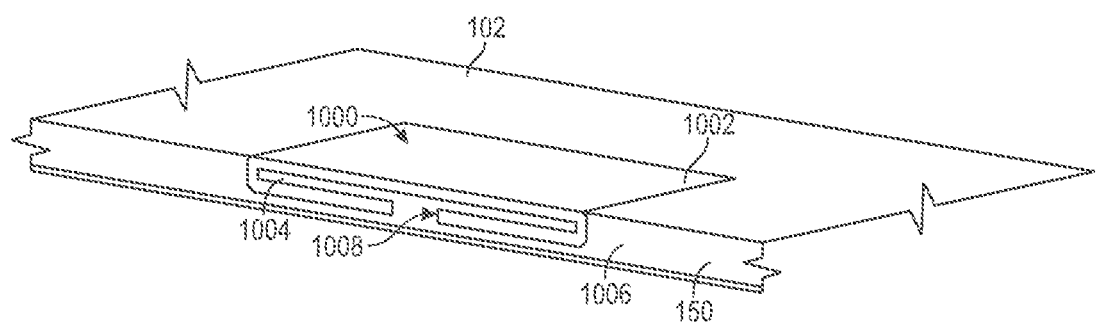
Figure 15C:
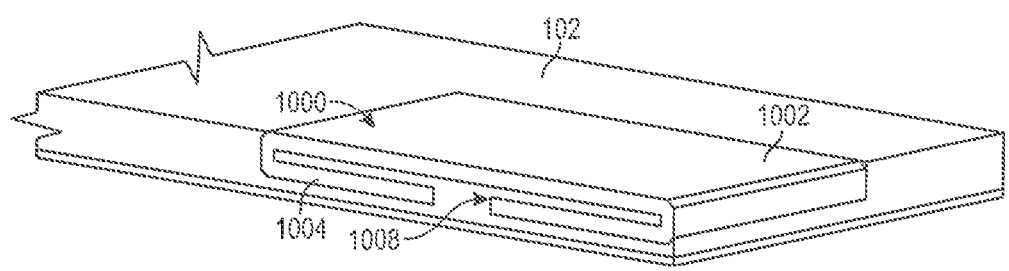

FIG. 15B shows electrode 1000 attached to sheath 102 at a position spaced from the distal tip 120 of the sheath. Both end portions 1004 and 1006 are bent toward one another against the inner surface of plate 1002 as described above. FIG. 15C is substantially the same as FIG. 15B. However, rather than being positioned at a spaced distance from the distal tip 120 of sheath 102, electrode 1000 in FIG. 15C is positioned at the distal tip of the sheath so that the end of the electrode is exposed on the distal end face of the sheath. As discussed above, assembling electrode 1000 to sheath 102 in this position produces the strongest signal from the bundle of His during a mapping procedure.

Figure 15D:
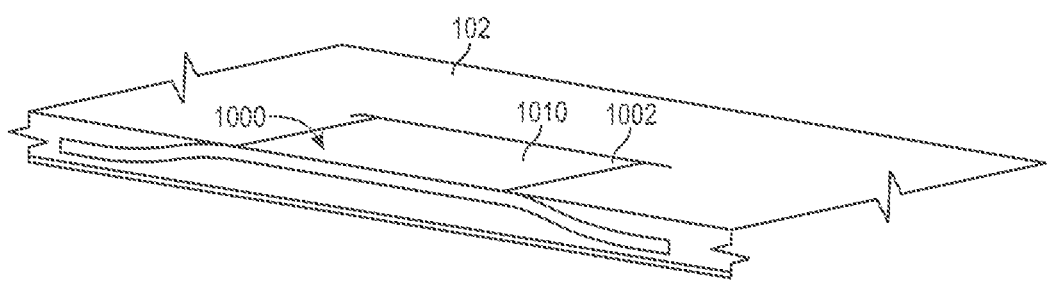

The configuration shown in FIG. 15D is similar to the configuration shown in FIG. 15A. However, rather than having one end portion bent toward the main body 1010 of plate 1002, both of end portions 1004 and 1006 are bent away from one another and away from main body 1010. Bending one or more of the end portions away from main body 1010, as shown in FIGS. 15A and 15D, facilitates the secure connection of electrode 1000 to sheath 102 as it does not require polymer to flow into the gaps 1008 between the end portions and the main portion 1010 of the electrode.

Electrode 1000 may also be affixed to sheath 102 in a variant of what has been described above in connection with FIGS. 13, 14, and 15A-15C. In each of those embodiments, at least one of end portions 1004 and 1006 is bent toward the inner surface of plate 1002, creating a gap 1008 between the end portion and the main body 1010 of the plate. In the variant contemplated, a separate strip of Pebax® or other polymer may be positioned against the inner surface of plate 1002 before the end portions are bent. Thus, after the bending operation, the strip of Pebax® or other polymer will be positioned in and fill gaps 1008. Electrode 1000 may then be assembled to sheath 102 as described above. However, during the reflow process, the sheath polymer will not have to fill gaps 1008, as those gaps will already have been filled. Rather, the polymer in gaps 1008 will melt and fuse to the other polymer of sheath 102, firmly holding electrode 1000 in place.

Figure 16:
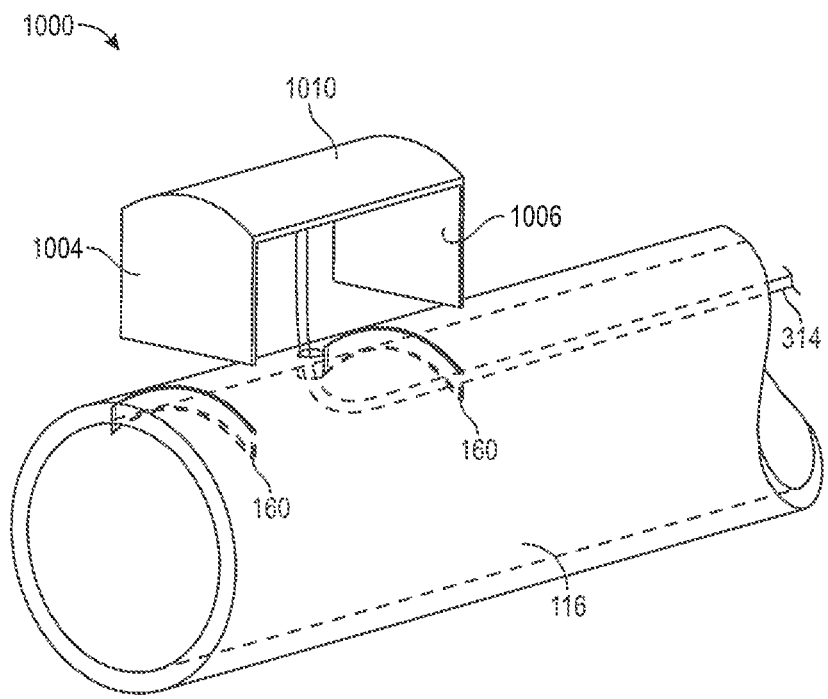
FIG. 16 is an exploded view showing a method of assembling the sheath electrode of FIG. 13 to a sheath.

Another technique for attaching electrode 1000 to sheath 102 is shown in FIG. 16. In this technique, distal section 124 of outer layer 114 is not assembled to sheath 102 during the sheath assembly process. Rather, slits 160 are formed at appropriate locations in section 124. The end portions 1004 and 1006 of electrode 1000 are then bent to an orientation orthogonal to the outer layer in main body 1010 of the electrode. Electrode 1000 may then be assembled to the distal section 124 of outer layer 114 by inserting end portions 1004 and 1006 into slits 160 and bending them against the inner surface of the sheath section. End portions 1004 and 1006 may be bent toward one another, away from one another, or one end portion may be bent toward the main body 1010, while the other end portion is bent away from the first end portion. With electrode 1000 assembled to section 124 as described, this section of outer layer 114 may be assembled over the distal end section 102d of sheath 102, which may again be subjected to a reflow heating process to melt and bond the distal section 124 of outer layer 114 to the underlying braided layer 112, trapping electrode 1000 in place.

In another variant for attaching any of the electrodes described above to sheath 102, the electrode may first be sandwiched between two strips of Pebax® or other polymer. The strip of polymer on the inner surface of the electrode may include an aperture for connecting a conductor 314 to the electrode. The sandwiched electrode assembly may then be properly positioned on sheath 102 and subjected to a reflow process through which the electrode is strongly affixed to the sheath. Following the reflow process, the outer layer of polymer covering the electrode may be removed by any known technique, including laser ablation, cutting, scraping, grinding and the like to expose the outer surface of the electrode.

When delivery device 100 is being used to map the location of the bundle of His 30, the free ends of conductors 314 may be connected through connector 340 to a patient monitor, electrocardiograph, or other external device for displaying the electrical signals detected by electrodes 310 and 312. Optionally, sheath 102 may include a ring electrode 350 (FIG. 5B) spaced proximally of mapping electrodes 310 and 312. As ring electrode 350 comprises a continuous ring, it may be incorporated in sheath 102 during assembly of the sheath, using techniques known in the art. In order to not interfere with the splitting or peeling of sheath 102 along its entire length, ring electrode 350 may be skived so as to readily separate into two when the sheath is being split and removed from the pacing lead, as described more fully below. The fabrication and use of skived rings that may be splittable is described in U.S. Pat. No. 8,449,527, the disclosure of which is hereby incorporated by reference herein. When ribs 111 extend radially to the outer surface of sheath 102, ring electrode 350 may be formed as two C-shaped sections positioned on opposite sides of the ribs in the same manner as electrodes 310 and 312. Electrical conductors (not shown) may extend from ring electrode 350 to connector 340 through tube 140 or through another tube incorporated in sheath 102. When available, voltage differences between ring electrode 350 and either of split electrodes 310 or 312 may be used to map the electrical activity of the heart.

Figure 17:
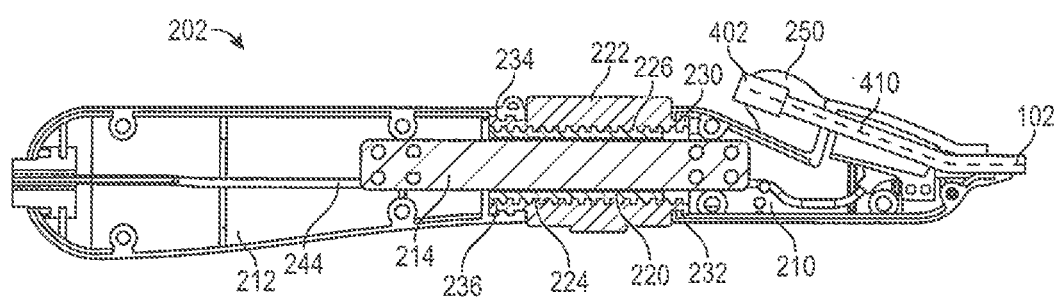
FIG. 17 is a longitudinal cross-section through the handle of the delivery device shown in FIG. 4.

Sheath 102 is connected at its proximal end to handle 202. A longitudinal cross-section of one embodiment of handle 202 is shown in FIG. 17. Handle 202 may include a distal housing portion 210 and a proximal housing portion 212, both of which are hollow. Housing portions 210 and 212 may be joined to one another by a rigid alignment rail 214 so as to maintain a space between the housing portions. Alignment rail 214 may be formed from a rigid material, such as glass-filled nylons, acetal homopolymers and copolymers, polycarbonate, polysulfone, etc., and may be connected to housing portions 210 and 212 by any known fastening mechanism, including screws, press fit connection, ultrasonic welding and the like. Prior to the connection of both ends of alignment rail 214 to the housing portions, a hollow pull wire screw 220 may be assembled over the rail and a rotatable actuator 222 may be assembled over the screw. Actuator 222 has a series of internal threads 224 that mate with external threads 226 on screw 220. At one end, actuator 222 has an annular ring 230 that is captured within an annular groove 232 in distal housing portion 210. At its other end, actuator 222 has a similar annular ring 234 that is captured within an annular groove 236 in proximal housing portion 212. The engagement of ring 230 in groove 232, and the engagement of ring 234 in groove 236, positions actuator 222 in the space between the housing portions, guides the rotation of the actuator in handle 202, and serves to help maintain the assembly of distal housing portion 210 to proximal housing portion 212. As actuator 222 is rotated in a first direction, pull wire screw 220 will translate proximally relative to handle 202, and when the actuator is rotated in the opposite direction, the pull wire screw will translate distally relative to the handle. The proximal end of pull wire 130 may be fed through pull wire screw 220 for connection in a known manner to the proximal end thereof. The distal end of pull wire 130 may be fed through narrow tube 132 of sheath 102 and welded to pull ring 134. Thus, as pull wire screw 220 translates proximally, it will translate pull wire 130 proximally, placing the pull wire in tension and resulting in the deflection of deflectable section 102c of sheath 102, and when pull wire screw 220 translates distally, it will translate pull wire 130 distally, leading to the movement of the pull wire and the deflectable section 102c of sheath 102 back to their initial and substantially straight positions.

Handle 202 may also include a conduit 240 having a connector 242 at its proximal end for connection to a source of flushing fluid (FIG. 4). Conduit 240 may be connected to a further conduit 244 (FIG. 17) that travels through handle 202 to hub 402 for supplying the flushing fluid to flush the interior of sheath 102. Conduit 320, carrying conductors 314, may be connected at one end to conduit 240 by a Y-splitter, and at the other end may be connected to electrical connector 340. Conductors 314, traveling from electrodes 310 and 312 through narrow tubes 140 of sheath 102, and through handle 202, exit therefrom through conduits 240 and 320, and are then connected by soldering or the like to pins in electrical connector 340.

Figure 18A:
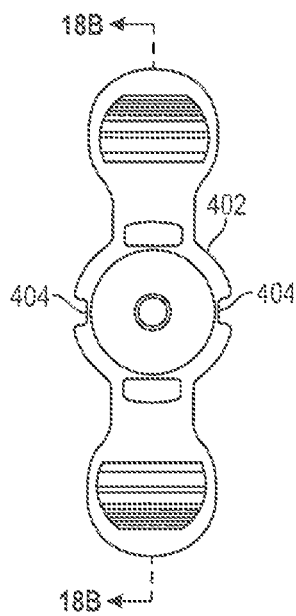
FIGS. 18A-B are a schematic end view and a highly schematic longitudinal cross-section, respectively, of a hub connected to a delivery device sheath.
Figure 18B:
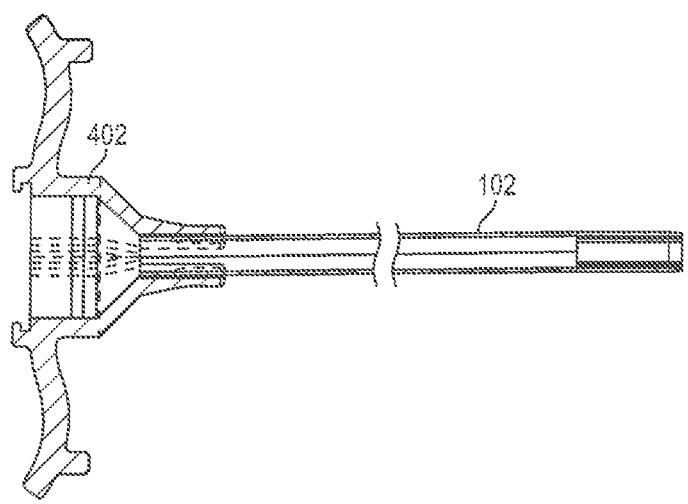

Referring to FIG. 17, hub 402 protrudes from the interior of distal housing portion 210 and fixedly connects the proximal end of sheath 102 to handle 202. In one arrangement, hub 402 may be injection molded around the proximal end of sheath 102. Hub 402 may be formed with thinned wall regions 404 that extend along the length of the hub in diametrically opposed portions of the hub, as shown in FIG. 18A. Hub 402 may be formed on or assembled to sheath 102 so that thinned regions 404 are aligned with ribs 111, enabling the hub and the sheath to be split along a continuous substantially straight line, shown as dashed line 410 in FIG. 17. Methods for forming a splittable hub are described in U.S. Pat. No. 7,377,909, the disclosure of which is hereby incorporated by reference herein. Sheath 102 may pass through a hemostasis valve (not shown) in or proximal of hub 402, which provides a seal to minimize blood loss from around the sheath. A web 250 of a polymer or other material may be formed around the exposed portion of hub 402 to firmly affix the hub to distal housing portion 210, and to provide a region on opposite sides of the hub that a user may grasp and pull to split the hub and sheath 102 longitudinally. Other configurations of delivery device 100 in which handle 202, hub 402 and connector 340 are in different positions relative to one another are contemplated herein and will be described further below.

Figure 19:
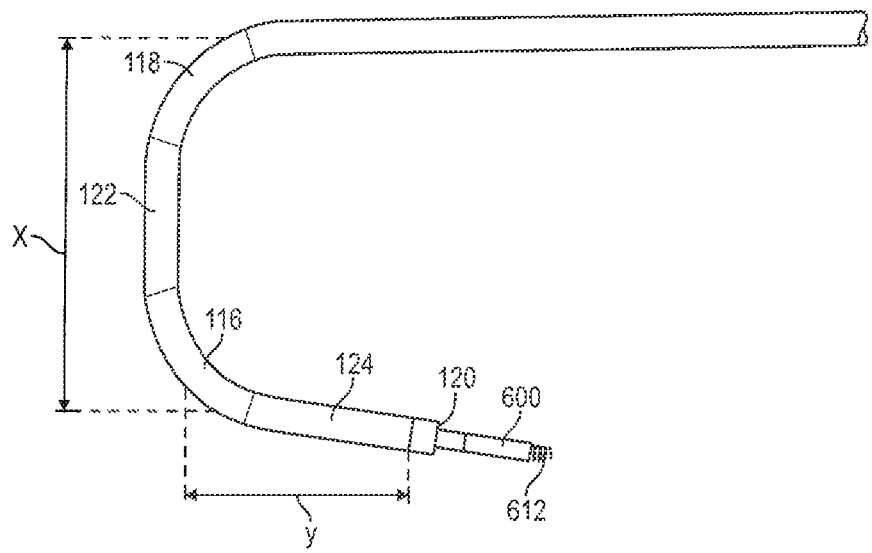
FIG. 19 is an enlarged view of the distal end of the delivery device sheath in a deflected condition.
Figure 20:
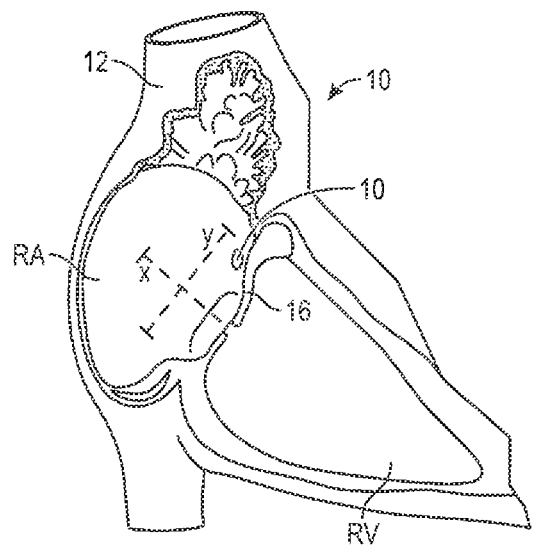
FIG. 20 is a diagrammatic view showing certain distances relative to structures in the heart.

When pull wire 130 is translated proximally, the pliability of sections 116 and 118 of outer layer 114 enables the deflectable section 102c of sheath 102 to deflect from a substantially straight configuration to the predefined dual hinged configuration shown in FIG. 19. By deflecting at these two spaced locations, sheath 102 assumes a shape that better enables its distal tip 120 to be positioned to confront the right atrial wall near His bundle 30 while the proximal section 102a of sheath 102 is positioned within the superior vena cava 12 of heart 10. Distance X in FIG. 19 is the average distance from the central axis of superior vena cava 12, through which sheath 102 enters the right atrium RA, to tricuspid valve 16, while distance Y is the average inner diameter of the tricuspid valve. One-third of distance Y approximates the distance which sheath 102 must traverse to reach the atrial wall in order to contact or come in close proximity to His bundle 30. As this distance is an approximation, and as exceeding this distance is not likely to have a negative effect on locating His bundle 30, it will be appreciated that this distance (which is approximately the distance from the section 122 of sheath 102 (or outer layer 114) to the distal tip 120 thereof) may be between about ⅓ Y and about ½ Y. Distances X and Y are illustrated relative to the structures of heart 10 in the diagrammatic illustration shown in FIG. 20. To complete the description, rotating actuator 222 in the opposite direction will translate pull wire 130 distally, returning sheath 102 toward the substantially straight configuration.

Figure 21:
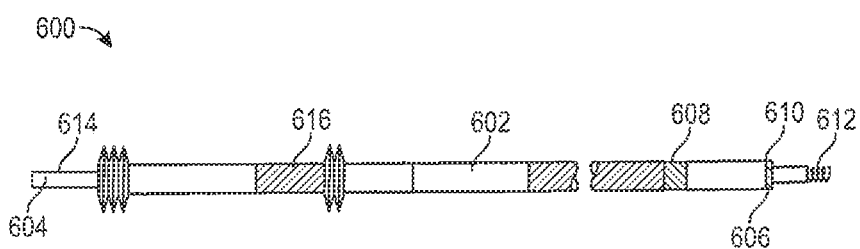
FIG. 21 is a highly schematic side view of a pacing lead.

Delivery device 100 may be used to deliver a pacing lead into the right atrium RA, to map the right atrium to locate His bundle 30, and to fix the pacing lead therein. One example of such a pacing lead is pacing lead 600 shown schematically in FIG. 21. Lead 600 generally has a flexible elongate body 602 with a proximal end 604, a distal end 606, and a lumen (not shown) extending axially therethrough. A pair of bipolar electrodes 608, 610 is located at the distal end of body 602. Electrode 610 is positioned at the distal tip of body 602, while electrode 608 may be spaced therefrom along the length of the body. A fixation anchor 612 extends distally from the distal end 606 of body 602 and forms a part of electrode 610. At the proximal end 604 of body 602, lead 600 includes a pair of electrical contacts 614 and 616. Contacts 614 and 616 are each electrically connected to one of electrodes 608 and 610 by conductors traveling through the lumen in body 602. Contacts 614 and 616 enable pacing lead 600 to be mechanically and electrically connected to pacemaker 52, such as by alligator clips or other connectors connected to contacts 614 and 616.

The use of delivery device 100 to deliver and fix pacing lead 600 in the bundle of His 30 will now be described with reference to FIGS. 22A-D and 23. FIGS. 22A-D illustrate the delivery and fixation of pacing lead 600 with respect to an anatomically-accurate transparent model 700 of the right side of the human heart. Model 700 may be used to train operators in the His pacing procedure, and to develop and test clinical tools for performing the procedure. For clarity, the reference numerals used in FIGS. 22A-D to identify the structures of the heart will be the same reference numbers used to identify the structures in the cutaway view of the heart illustrated in FIG. 1. The region in which the bundle of His is located is simulated in model 700 by a conductive insert (not shown) that may be received in port 710. The insert may be formed of a gel to enable fixation of pacing lead 600 therein and may have physical and/or electrical properties that simulate myocardial tissue. The insert may also be doped with an ionic material to provide electrical properties similar to those of the His bundle so that electrically-active delivery devices can be used to map the region. During a mapping and fixation procedure, the insert may be stimulated electrically by a circuit to produce an electric signal, preferably one that is similar to that produced by the bundle of His. A more detailed description of model 700 and its use can be found in commonly owned patent application Ser. No. 16/208,348, the disclosure of which is hereby incorporated by reference herein.

Figure 22A:
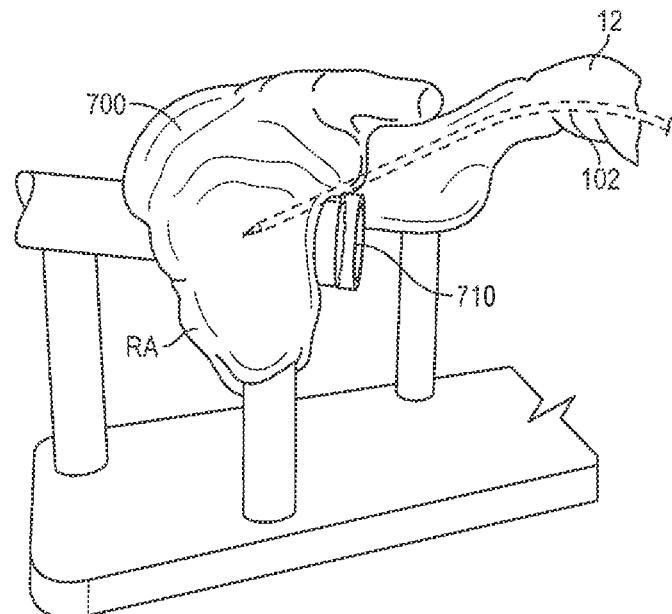
FIGS. 22A-D illustrate an in vitro process by which the delivery device of FIG. 4 locates the bundle of His and implants a pacing lead therein.
Figure 22B:
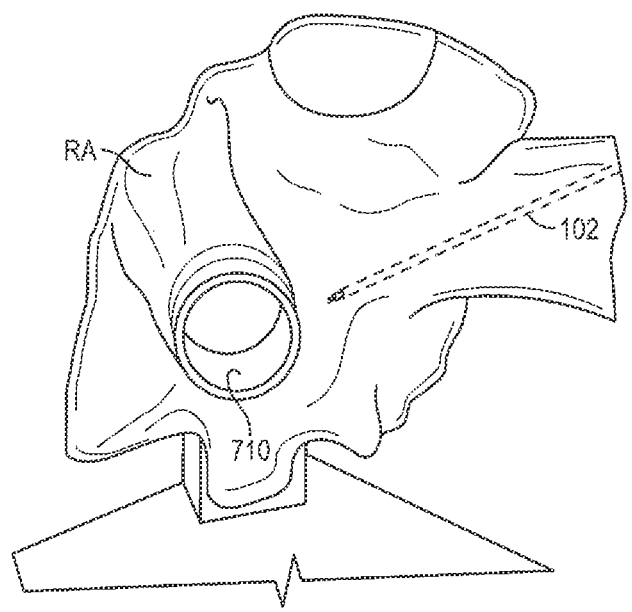

With conductors 314 electrically connected through connector 340 to an external device for receiving signals from electrodes 310 and 312, delivery device 100 is inserted through a vascular access site into the superior vena cava 12 and is maneuvered through the superior vena cava to the right atrium RA as illustrated in FIGS. 22A and 22B. During this insertion procedure, the sheath 102 of delivery device 100 may have a substantially straight configuration and may include a dilator (not shown) positioned in the lumen 126 thereof to enlarge the access path and to provide support to the sheath as it is being maneuvered. The straight configuration of sheath 102 facilitates its passage through the superior vena cava 12 and into the right atrium RA. Once the distal tip 120 of delivery device 100 has entered the right atrium RA, the dilator may be removed from the delivery device and pacing lead 600 may be inserted into lumen 126 in its place. Again, the straight configuration of sheath 102 facilitates the insertion of pacing lead 600 therein.

Figure 22C:
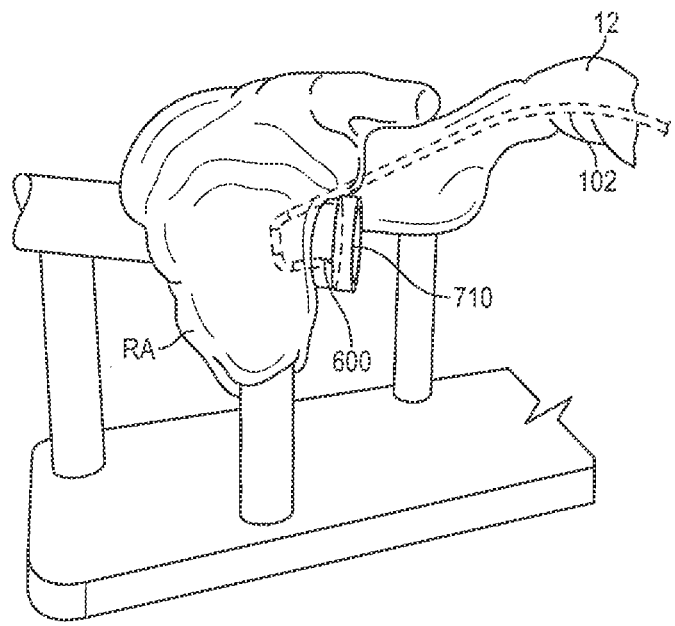
Figure 22D:
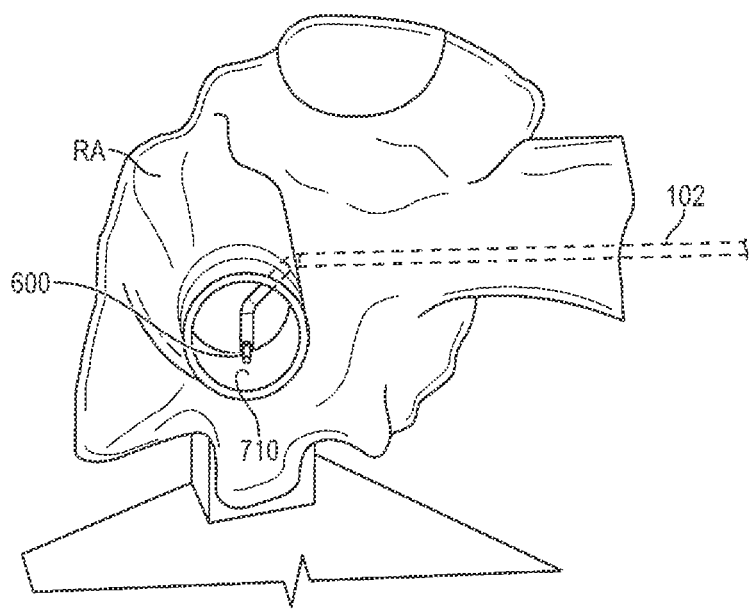

With the distal portion of sheath 102 fully within right atrium RA, the user may operate delivery device 100 to place sheath 102 in the deflected configuration shown in FIG. 22C. Since sheath 102 is only able to deflect in a single direction, the user must first confirm that delivery device 100 is in the proper orientation. This may be accomplished by locating the position of indicia (not shown) in the proximal section 102a of sheath 102 or on handle 202, by the nonsymmetrical shape of the handle or by another indicator. Such indicator preferably will identify the side of sheath 102 on which pull wire 130 is located, which is the direction to which the deflectable section 102c of the sheath will deflect. Once the proper orientation of sheath 102 has been confirmed, the user may operate the actuator 222 on the handle 202 of delivery device 100 to move the deflectable section 102c of the sheath to the deflected configuration. With the proximal section 102a of sheath 102 positioned in the superior vena cava 12 and the deflectable section 102c of the sheath deflected as shown in FIG. 22C, the distal tip 120 of the sheath will point generally toward the region in the atrial septum at which the bundle of His 30 is located, and will be in close proximity to the septum, as shown in FIG. 22D. If electrical signals are received from electrodes 310 and 312 in this position of sheath 102, the user will know that the distal tip 120 of the sheath is aligned with His bundle 30.

If electrodes 310 and 312 are not receiving electrical signals, or if the signals are very faint, the user may maneuver the distal tip 120 of sheath 102 by small movements of actuator 222 in either a forward or reverse direction to scan the atrial wall. These small movements of actuator 222 will deflect the deflectable section 102c of sheath 102 by small amounts toward or away from the proximal section 102a of the sheath. Scanning in different directions can be accomplished by small rotations of handle 202, which rotates the distal end section 102d of sheath 102 about the longitudinal axis of the sheath. When the signals received by electrodes 310 and 312 are the strongest, the user can be confident that His bundle 30 has been located, and the close proximity of the electrodes to one another will assure that the His bundle is directly opposite the distal tip 120 of sheath 102. With each of these movements, the distal tip 120 of sheath 102 remains generally perpendicular to the atrial wall. Accordingly, once this mapping procedure has located the bundle of His, pacing lead 600 can be fixed in the His bundle by advancing the fixation anchor 612 of the lead out from the distal tip 120 of sheath 102 and rotating the lead within delivery device 100 to drive the fixation anchor into the atrial septal wall, as shown schematically in FIG. 22. Since the overall stiffness of sheath 102 is relatively high, the distal tip of the sheath will maintain its position as fixation anchor 612 is driven into the atrial septal wall, thereby assuring that the fixation anchor will not be diverted from its target site.

Once lead 600 has been properly fixed in the tissue of the bundle of His, sheath 102 may be returned to a substantially straight configuration by rotating actuator 222 in the direction opposite that used for deflection. Sheath 102 may then be removed from around lead 600 and from heart 10. This may be accomplished by pulling the opposite sides of hub 402 away from one another to separate the hub along thinned regions 404. Continued pulling of the sides of hub 402 away from one another will cause the sides of sheath 102 on opposite sides of ribs 111 to move away from one another to split the sheath in half along its length. After hub 402 and an initial length of sheath 102 has been split in half, the user may apply forward pressure to pacing lead 600 while pulling the sheath proximally to expose a next length of the sheath. This next length of sheath 102 may then be split in two by pulling the sides of the sheath in opposite directions. The user may then again apply forward pressure to pacing lead 600 while withdrawing a further length of sheath 102 proximally. This process may be continued until sheath 102 has been split into two along its entire length and removed from lead 600, leaving the lead embedded within the atrial septal wall at the bundle of His.

Although the sheath 102 of delivery device 100 has been described as including a liner 110 having square or rectangular ribs 111 that are covered by outer layer 114, it is contemplated that liner 110 may have one or more ribs with a variety of different shapes and/or sizes, and these ribs may extend to the outer surface of the sheath, may be covered by outer layer 114, or may have other configurations. Cross-sections of sheath 102 having at least some of these different configurations are shown in FIGS. 7A-7K.

FIG. 7A shows the cross-section of a sheath 102.1 that is substantially the same as that of sheath 102 shown in FIG. 5C. However, rather than having outer layer 114 formed as a complete tube with recesses 115 for mating with ribs 111, the outer layer of sheath 102.1 is thinner than that of sheath 102 and is formed as two C-shaped sections 114a and 114b that are assembled to the sheath on opposite sides of ribs 111. As a result, ribs 111 may extend to the outer surface of sheath 102.1. While this configuration may require additional assembly steps not required for the configuration of sheath 102 shown in FIGS. 5A-C, the fact that ribs 111 are exposed on the outer surface of sheath 102.1 provides improved peelability over that of sheath 102.

The configuration of sheath 102.2 shown in FIG. 7B is similar to that of sheath 102.1 shown in FIG. 7A. However, the C-shaped outer sections 114a and 114b of sheath 102.2 have a thickness that is similar to the thickness of outer layer 114 in sheath 102. Rather than extrude a very thin section of outer layer 114 overlying ribs 111, separate strips of material 119 overlapping the ribs may be coextruded with the outer layer. Strips of material 119 may be formed of similar polymer materials to those used to form outer layer 114, but they generally have some desirable material properties, e.g. improved peelability and/or surface lubricity.

As noted above, it is desirable to have sheath 102 bend smoothly when deflected during use. However, it is known that the PTFE liner 110 with ribs may have a tendency to kink when bent because of its limited mechanical strength.

This may also cause the deflection of the sheath to not occur in a plane. The configuration of sheath 102.3 shown in FIG. 7C addresses these issues by providing a reinforcing ribbon 121 on each side of ribs 111 along the length of the sheath, or at least along the length of deflectable section 102c. Ribbons 121 may be formed from stainless steel or high-performance engineering polymers including, but not limited to, polyetherimide, aromatic polyamides, polysulfones, polyether sulfones, aromatic polyesters and liquid crystal polymers. Aside from ribbons 121, sheath 102.3 has substantially the same configuration as sheath 102 of FIG. 5C.

The configuration of sheath 102.4 shown in FIG. 7D is substantially the same as the configuration of sheath 102.1 described above. However, sheath 102.4 incorporates reinforcing ribbons 121 on either side of ribs 111 along the length of the sheath, or at least along the length of deflectable section 102c. Similarly, the configuration of sheath 102.5 shown in FIG. 7E is substantially the same as the configuration of sheath 102.2 shown in FIG. 7B but includes reinforcing ribbons 121 on the sides of ribs 111 along the length of the sheath or at least along the length of deflectable section 102c.

Figure 7F:
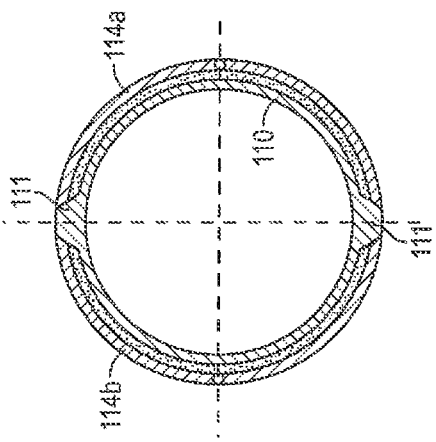
Figure 7G:
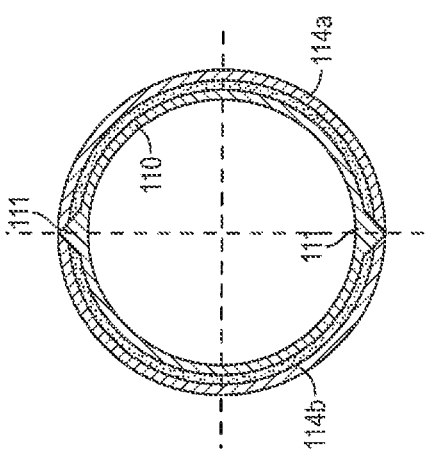
Figure 7H:
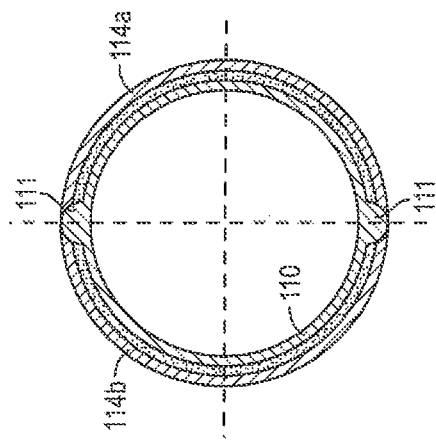
Figure 7I:
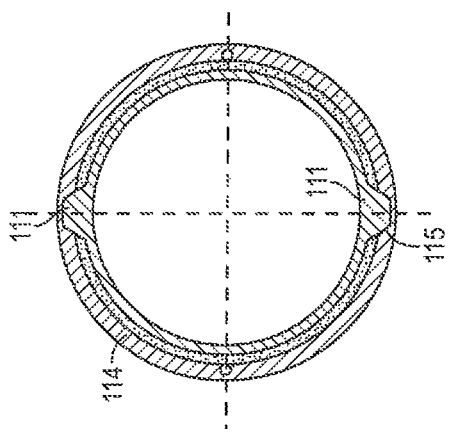
Figure 7J:
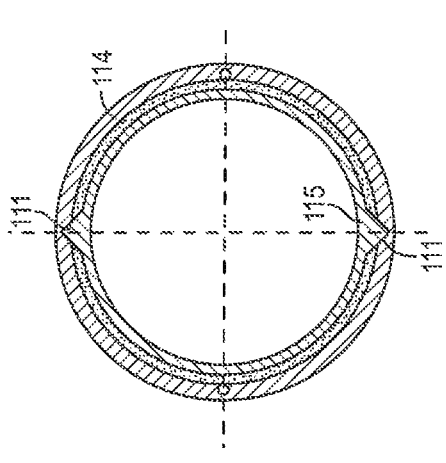
Figure 7K:
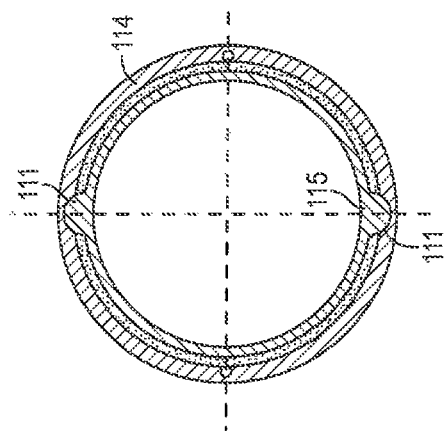

It is also contemplated that the ribs 111 in sheath 102 may have a shape that is other than square or rectangular. Thus, FIG. 7F shows a sheath in which ribs 111 are trapezoidal, FIG. 7G shows a sheath in which ribs 111 are triangular, and FIG. 7H shows a sheath in which ribs 111 are semi-circular. In each of these configurations, the outer layer of the sheath is formed as two C-shaped sections 114a and 114b that are assembled to the sheath on opposite sides of ribs 111, the ends of the C-shaped sections being shaped to correspond to and mate with the shape of the ribs. The ribs 111 in these embodiments extend to the outer surface of the sheath. FIGS. 7I, 7J and 7K illustrate sheaths having trapezoidal, triangular and semi-circular ribs 111, respectively, but include an outer layer 114 that is formed as a continuous tube having one or more inner recesses 115 that correspond to the shape and size of the ribs.

Figure 24A:
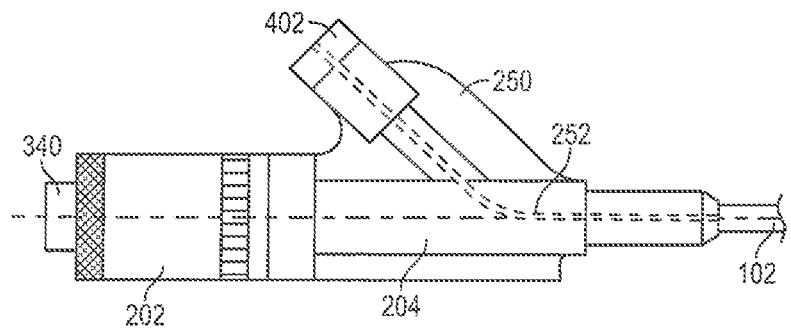
FIGS. 24A-C are highly schematic side views of the proximal end of various embodiments of a pacing lead delivery device, including the handle, the hub and the electrical connector.

As noted, it is contemplated that delivery device 100 may be configured differently, with handle 202, hub 402 and electrical connector 340 arranged in different relative positions than described above. Various configurations of delivery device 100 are shown schematically in FIGS. 24A-C. FIG. 24A is a highly schematic view of an embodiment of delivery device 100 that is very similar to that shown in FIG. 4. In the delivery device of this embodiment, sheath 102 enters a splittable tubular structure 204 at the distal end of handle 202 in an orientation that is coaxial with the handle. Tubular structure 204 may be formed in a manner similar to hub 402, e.g., with thinned walls in the regions along which the tubular structure is to split. As shown in FIG. 24A, tubular structure 204 may not split apart along its entire length but may split apart only partially along its length. Sheath 102 then curves toward a splittable hub 402 at the top of handle 202. Hub 402 is secured to handle 202 by web 250, which provides a region on opposite sides of the hub for a user to grasp and pull apart to split the hub, tubular structure 204 and sheath 102 longitudinally along a split line or split plane, shown as the heavy line 252. Electrical connector 340 is positioned at the proximal end of handle 202. Connector 340 may be oriented at an oblique angle to handle 202, as shown in FIG. 4, or may be colinear with the handle, as shown in FIG. 24A.

Figure 24B:
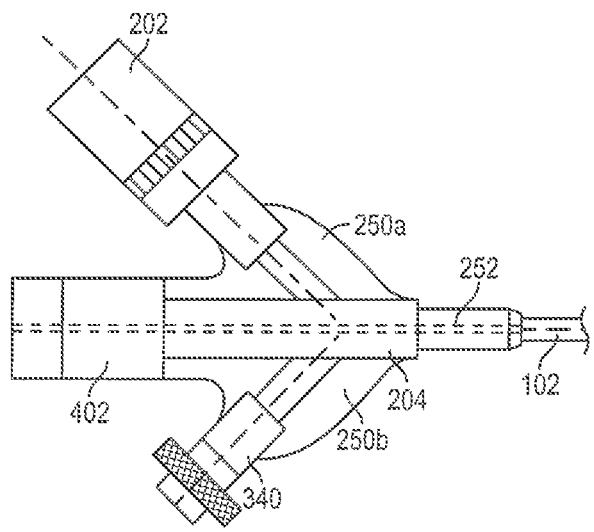

An alternate embodiment of delivery device 100 is shown in FIG. 24B. In this embodiment, handle 202 extends at an oblique angle from the top of splittable tubular structure 204, while electrical connector 340 extends at a similar oblique angle from the bottom of the tubular structure. A first web 250a secures handle 202 to tubular structure 204, and a second web 250b secures electrical connector 340 to the tubular structure. Splittable hub 402 is positioned at the proximal end of tubular structure 204. To remove sheath 102 from pacing lead 600 in this embodiment, the user may grasp opposite sides of hub 402, pulling them away from one another to split the hub, tubular structure 204 and then sheath 102 longitudinally along split line or split plane 252. This embodiment enables forward pressure to be applied to pacing lead 600 in a linear direction and sheath 102 to be retracted in a linear direction as the splitting of the sheath advances along its length.

Figure 24C:
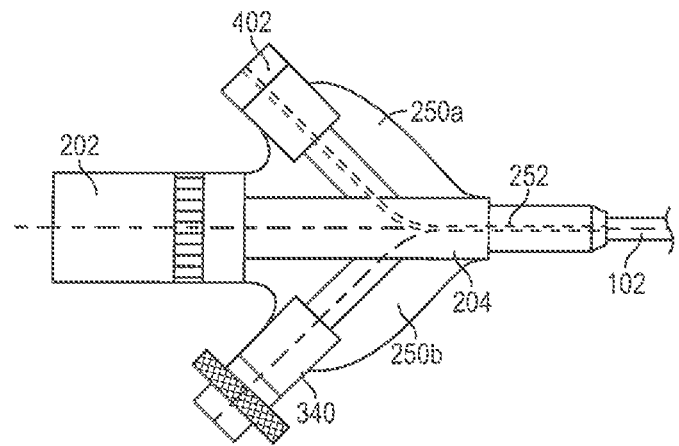

The embodiment of FIG. 24C is similar to the embodiment of FIG. 24A. However, rather than having electrical connector 340 positioned at the proximal end of handle 202 coaxially with the handle, the connector in FIG. 24C projects at an oblique angle from the bottom of splittable tubular structure 204. A first web 250a secures splittable hub 402 to tubular structure 204, while a second web 250b secures electrical connector 340 to the tubular structure. To remove sheath 102 from pacing lead 600 in this embodiment, the user may grasp and pull apart opposite sides of hub 402, tubular structure 204 and sheath 102 along split line 252.

To summarize the foregoing, according to a first aspect of the disclosure, a delivery device for delivering a pacing lead to the His bundle of a patient's heart includes a handle; an elongated sheath having a proximal end connected to the handle and a distal end remote from the handle, a distal portion of the sheath having a plurality of flexible sections spaced from one another along a length of the sheath, the sheath having a longitudinal rib extending from the proximal end to the distal end and being splittable along a first split line from the proximal end to the distal end; a pull wire having a distal end connected to the sheath distally of the flexible sections and extending to a proximal end; and a plurality of mapping electrodes positioned at the distal end of the sheath; and or the distal end of the sheath may have a distal tip, and the mapping electrodes may include two electrodes positioned on opposite sides of the rib at positions spaced from the distal tip of the sheath; and/or the two electrodes may be spaced apart by between about 1 mm and about 3 mm in a circumferential direction of the sheath; and/or the distal end of the sheath may have a distal end face, and the mapping electrodes may be exposed on the distal end face; and/or the distal end of the sheath may have a distal end face, and the mapping electrodes may be spaced from the distal end face; and/or the flexible portions of the sheath may have a first Shore D hardness which is less than a second Shore D hardness of remaining portions of the sheath; and/or the flexible portions of the sheath may have a Shore D hardness of between about 20 and about 40; and/or the flexible portions of the sheath may have a Shore D hardness of about 35; and/or the remaining portions of the sheath may have a Shore D hardness of between 60 and about 100; and/or the remaining portions of the sheath may have a Shore D hardness of between 70 and about 75; and/or the delivery device may further include a hub at the proximal end of the sheath, the hub having a weakened region defining a second split line longitudinally aligned with the first split line in the sheath; and/or the handle may include a rotatable portion and a translatable portion, the proximal end of the pull wire being connected to the translatable portion, whereby rotation of the rotatable portion translates the pull wire in a longitudinal direction of the sheath; and/or the handle may include a proximal handle portion and a distal handle portion, the proximal handle portion being connected to the distal handle portion by a rail so as to define a space between the proximal handle portion and the distal handle portion; and/or the handle may include a rotatable actuator positioned in the space and connected to the proximal handle portion and the distal handle portion, rotation of the actuator in a first direction bending the flexible sections of the sheath toward a dual hinged configuration and rotation of the actuator in an opposite direction moving the sheath toward a substantially straight configuration; and/or the handle may have a longitudinal axis and the proximal end of the sheath may enter the handle along the longitudinal axis and may exit the handle at an angle transverse to the longitudinal axis; and/or the handle may have a longitudinal axis and the proximal end of the sheath may enter the handle at a predetermined angle transverse to the longitudinal axis and may exit the handle at the predetermined angle transverse to the longitudinal axis; and/or each of the mapping electrodes may include a pair of side edges substantially parallel to a longitudinal axis of the sheath and a pair of end edges substantially orthogonal to the longitudinal axis of the sheath, and the side edges may be beveled; and/or each of the electrodes may be formed from a plate having a pair of opposed side edges and a pair of opposed end edges, and the plate may have a thickness along the side edges and along the end edges that is less than the thickness in a center of the plate; and/or each of the electrodes may have a main body and a pair of end portions projecting from opposite ends of the main body; and/or the end portions may project away from the main body in opposite directions; and/or the main body may have an inner surface and an outer surface, and at least one of the end portions may be bent against the inner surface of the main body; and/or the pair of end portions may be bent toward one another and toward the inner surface of the main body; and/or the sheath may include an inner layer or liner, a middle or braided layer, and an outer layer, the longitudinal rib being formed on the inner layer and extending through the middle layer; and/or the longitudinal rib may extend through the outer layer; and/or the inner layer may extend from the proximal end of the sheath to the distal end of the sheath; and/or the inner layer may be formed from a lubricious material; and/or the lubricious material may be polytetrafluoroethylene; and/or the inner layer may include platelet-like fibrils oriented in a longitudinal direction of the sheath; and/or the middle layer may be a braided layer including metallic braids embedded within a polymer; and/or the braided layer may extend from the proximal end of the sheath to the distal end of the sheath; and/or the outer layer may include a plurality of sections formed from a polymer having a first shore D hardness and a plurality of sections formed from a polymer having a second shore D hardness which is greater than the first shore D hardness; and/or the dual hinged configuration of the sheath may define a deflection plane, and the mapping electrodes may include two electrodes that are positioned on the sheath so that the two electrodes lie within the deflection plane in the dual hinged configuration; and/or the sheath may have a second longitudinal rib extending from the proximal end to the distal end, the second longitudinal rib being diametrically opposed to the first longitudinal rib, the sheath being splittable along another split line from the proximal end to the distal end.

According to another aspect of the disclosure, a method for delivering a pacing lead to the His bundle of a patient's heart includes providing a delivery device having a sheath with a proximal end, a distal end, a rib extending from the proximal end to the distal end, an axial lumen and a distal end face; inserting the sheath into the patient's body through the superior vena cava until a distal end section of the sheath is positioned in the right atrium of the patient; inserting a pacing lead into the axial lumen of the sheath; deflecting the distal end section of the sheath so that the distal end face of the sheath confronts the wall of the right atrium; moving the distal end face of the sheath relative to the wall of the right atrium until electrodes adjacent the distal end face of the sheath receive electrical signals from the His bundle; fixing the pacing lead to tissue at the His bundle; and splitting the sheath along a first split line from the proximal end to the distal end to remove the sheath from the pacing lead; and/or the delivery device may include a handle connected to a proximal end of the sheath and a pull wire extending from the handle to a distal end section of the sheath, and the deflecting step may include translating the pull wire proximally relative to the handle; and/or the handle may include a rotatable actuator, and the deflecting step may include rotating the actuator in a first direction to move the pull wire proximally relative to the handle; and/or the distal end portion of the sheath may include a plurality of flexible sections spaced from one another along a length of the sheath, and the deflecting step may include bending the sheath at the flexible sections to place the distal end section of the sheath in a dual hinged curved configuration; and/or the method may further include the step of fixing the pacing lead to tissue in the bundle of His.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, although the delivery device has been described herein for use in mapping the bundle of His and fixing a pacing lead therein, the delivery device may also be used as a component of an ablation catheter to ablate the bundle of His. In such event, the heart could be paced using multiple leads in various chambers of the heart.

What is claimed is:

1. A delivery device for delivering a lead to a patient's heart, the delivery device comprising:
   a handle; and
   an elongated sheath comprising:

a proximal end connected to the handle and a distal end remote from the handle;

a distal portion of the sheath having a plurality of flexible sections spaced from one another along a length of the sheath;

a first layer having a longitudinal rib that protrudes radially outward from an outer surface of the first layer, the longitudinal rib extending along the length of the sheath;

a first split line extending along the sheath; and a second layer surrounding the first layer, the second layer having a recess facing radially inward and mating with the rib, the first split line aligned with the rib and the recess to facilitate splitting of the sheath.

2. The delivery device of claim 1, further comprising a plurality of mapping electrodes positioned at the distal end of the sheath, wherein the plurality of mapping electrodes comprise two electrodes that are spaced between 1 mm and 3 mm in a circumferential direction of the sheath.

3. The delivery device of claim 2, wherein the distal end of the sheath has a distal end face, and the mapping electrodes are exposed on the distal end face.

4. The delivery device of claim 1, wherein the longitudinal rib extends from the proximal end to the distal end, the sheath being splittable along the first split line from the proximal end to the distal end.

5. The delivery device of claim 1, wherein the flexible sections of the sheath have a Shore D hardness of between 20 and 40.

6. The delivery device of claim 5, wherein the flexible sections of the sheath have a Shore D hardness of 35.

7. The delivery device of claim 5, wherein remaining sections of the sheath have a Shore D hardness of between 60 and 100.

8. The delivery device of claim 7, wherein the remaining sections of the sheath have a Shore D hardness of between 70 and 75.

9. The delivery device of claim 1, further comprising a hub at the proximal end of the sheath, the hub having a weakened region defining a second split line longitudinally aligned with the first split line in the sheath.

10. The delivery device of claim 1, wherein the delivery device is configured to position the distal end of the sheath proximate at least one of a HIS bundle, a position along a septum wall proximate to a left bundle branch, or a position along the septum wall proximate to a right bundle branch.

11. The delivery device of claim 1, wherein the distal portion of the sheath is configured to pass through a vascular access site into a right atrium (RA) and the pull wire is configured to deflect the distal portion of the sheath to locate the distal end of the sheath proximate to a His bundle.

12. The delivery device of claim 1, wherein the handle includes a proximal handle portion and a distal handle portion, the proximal handle portion being connected to the distal handle portion by a rail to define a space between the proximal handle portion and the distal handle portion.

13. The delivery device of claim 12, further comprising a rotatable actuator positioned in the space and connected to the proximal handle portion and the distal handle portion, rotation of the actuator in a first direction bending the flexible sections of the sheath toward a dual hinged configuration and rotation of the actuator in an opposite direction moving the sheath toward a substantially straight configuration.

14. The delivery device of claim 1, wherein the sheath has a second longitudinal rib extending along the length of the sheath, the second longitudinal rib being diametrically opposed to the first longitudinal rib, the sheath being splittable along a second split line, the second split line aligned with the second longitudinal rib.

15. The delivery device of claim 14, wherein the second longitudinal rib extends from the proximal end to the distal end, and the sheath is splittable along the second split line from the proximal end to the distal end.

16. The delivery device of claim 1, wherein the first layer is formed from polytetrafluorethylene.

17. The delivery device of claim 1, wherein the first and second layers represent inner and outer layers, the sheath further including a middle layer, the longitudinal rib extending through the middle layer.

18. The delivery device of claim 1, wherein the sheath includes at least two of the inner layer, a middle layer and the outer layer, the rib extending along one of the inner layer or middle layer, the recess provided in another of the middle layer or outer layer, the rib and recess mating with one another.

19. The delivery device of claim 1, further comprising a pull wire having a distal end connected to the sheath distally of the flexible sections and extending to a proximal end.

20. The delivery device of claim 19, further comprising a plurality of mapping electrodes positioned at the distal end of the sheath, wherein the pull wire is configured to deflect the distal portion of the sheath to locate the plurality of mapping electrodes proximate to a His bundle of the patient's heart.

* * * * *